United States Patent

Bagley et al.

[11] Patent Number: 5,151,435
[45] Date of Patent: Sep. 29, 1992

[54] ANGIOTENSIN II ANTAGONISTS INCORPORATING AN INDOLE OR DIHYDROINDOLE

[75] Inventors: Scott Bagley, Rahway; William J. Greenlee, Teaneck; Daljit S. Dhanoa, Tinton Falls; Arthur A. Patchett, Westfield, all of N.J.

[73] Assignee: Merck & Co., Inc., Rahway, N.J.

[21] Appl. No.: 681,793

[22] Filed: Apr. 8, 1991

[51] Int. Cl.$^5$ .................. A61K 31/435; C07D 470/04
[52] U.S. Cl. ..................................... 514/303; 514/81; 514/234.2; 544/127; 546/22; 546/118
[58] Field of Search .................. 546/118, 22; 514/303, 514/81, 234.2

[56] References Cited

FOREIGN PATENT DOCUMENTS

| | | |
|---|---|---|
| 58696/7 | 7/1989 | Australia . |
| 0260613 | 9/1987 | European Pat. Off. . |
| 0400974 | 5/1990 | European Pat. Off. . |
| 0411766 | 6/1990 | European Pat. Off. . |
| 409332 | 7/1990 | European Pat. Off. . |
| 0415886 | 8/1990 | European Pat. Off. . |
| 0419048 | 8/1990 | European Pat. Off. . |
| 0429257 | 11/1990 | European Pat. Off. . |
| 0430709A2 | 11/1990 | European Pat. Off. . |

Primary Examiner—Bernard Dentz
Attorney, Agent, or Firm—Joseph F. DiPrima; William H. Nicholson; Valerie J. Camara

[57] ABSTRACT

There are disclosed substituted indoles and dihydroindoles of Formula I which are useful as angiotensin II antagonists.

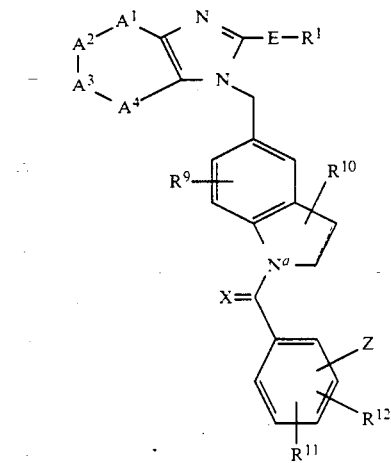

10 Claims, No Drawings

ANGIOTENSIN II ANTAGONISTS INCORPORATING AN INDOLE OR DIHYDROINDOLE

BACKGROUND OF THE INVENTION

The Renin-angiotensin system (RAS) plays a central role in the regulation of normal blood pressure and seems to be critically involved in hypertension development and maintenance as well as congestive heart failure. Angiotensin II (A II), is an octapeptide hormone produced mainly in the blood during the cleavage of angiotensin I by angiotensin converting enzyme (ACE) localized on the endothelium of blood vessels of lung, kidney, and many other organs. It is the end product of the renin-angiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by partial agonist activity and lack of oral absorption [M. Antonaccio. *Clin. Exp. Hypertens.* A4, 27-46 (1982); D. H. P. Streeten and G. H. Anderson, Jr.-*Handbook of Hypertension, Clinical Pharmacology of Antihypertensive Drugs*, ed. A. E. Doyle, Vol. 5, pp. 246-271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; and 4,582,847 in European Patent Applications 028,834; 245,637; 253,310; and 291,969; and in articles by A. T. Chiu, et al. [*Eur. J. Pharm. Exp. Therap*, 157, 13-21 (1988)] and by P. C. Wong, et al. [*J. Pharm. Exp. Therap*, 247, 1-7 (1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

None of the compounds disclosed in this application have been identified in any U.S. Patent, European Applications or articles. The substituted imidazoles, have been disclosed in patents to DuPont (EPO 253,310 and EPO 324,377) focusing on the design of Angiotensin II Antagonists. Substituted benzimidazole containing compounds useful as angiotensin II antagonists have been disclosed in U.S. Pat. No. 4,880,804 and European Patent Application 392,317. Substituted imidazopyridine containing compounds useful as angiotensin II antagonists have also been disclosed in European Patent Applications 260,613, 399,731 and 412,848 and U.S. Ser. No. 516,286 (filed May 4, 1990).

BRIEF DESCRIPTION OF THE INVENTION

The compounds of Formula (I) are angiotensin II antagonists and are useful in the treatment of hypertension and congestive heart failure. Additionally, pharmaceutically acceptable compositions of these novel compounds, as the sole therapeutically active ingredient and in combination with diuretics and other antihypertensive agents, including beta-blockers, angiotensin converting enzyme inhibitors, calcium channel blockers or a combination thereof are disclosed. Further, methods of treating hypertension, congestive heart failure and elevated intraocular pressure are described and claimed.

The compounds of this invention have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

DETAILED DESCRIPTION OF THE INVENTION

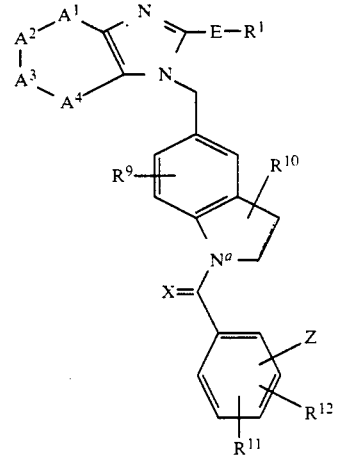

wherein:
$R^1$ is:
(a) $(C_1-C_6)$-alkyl, $(C_2-C_6)$-alkenyl or $(C_2-C_6)$-alkynyl each of which can be unsubstituted or substituted with a substituent selected from the group consisting of:
 i) aryl as defined below in $R^1$ (b),
 ii) $(C_3-C_7)$-cycloalkyl,
 iii) Cl, Br, I, F,
 iv) OH,
 v) $NH_2$,
 vi) $NH(C_1-C_4)$-alkyl,
 vii) $N[((C_1-C_4)$-alkyl$)]_2$,
 viii) $NHSO_2R^2$,
 ix) $CF_3$,
 x) $COOR^2$, or
 xi) $SO_2NHR^{2a}$; and
(b) aryl, wherein aryl is defined as phenyl or naphthyl, unsubstituted or substituted with 1 or 2 substituents selected from the group consisting of:
 i) Cl, Br, I, F,
 ii) $(C_1-C_4)$-alkyl,
 iii) $(C_1-C_4)$-alkoxy,
 iv) $NO_2$
 v) $CF_3$
 vi) $SO_2NR^{2a}R^{2a}$,
 vii) $(C_1-C_4)$-alkylthio,
 viii) hydroxy,
 ix) amino,
 x) $(C_3-C_7)$-cycloalkyl,
 xi) $(C_3-C_{10})$-alkenyl; and (c) heteroaryl, wherein heteroaryl is defined as a 5- or 6-membered heteroaromatic moiety, which can contain one or two members selected from the group consisting of N, O, S and wherein the heteroaryl is optionally mono- or disubstituted with substituents selected from the group consisting of:
  i) Cl, Br, I, F,
  ii) OH,
  iii) SH,
  iv) $NO_2$,
  v) $(C_1-C_4)$-alkyl,
  vi) $(C_2-C_4)$-alkenyl,
  vii) $(C_2-C_4)$-alkynyl,
  viii) $(C_1-C_4)$-alkoxy, or
  ix) $CF_3$,
(d) $(C_1-C_4)$-perfluoroalkyl,
(e) $(C_3-C_8)$-cycloalkyl, or
(f) $(C_1-C_4)$-alkyl-$(C_3-C_8)$-cycloalkyl;

—$A^1$—$A^2$—$A^3$—$A^4$— is:

(a)
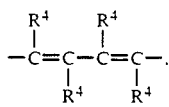

(b)
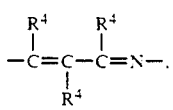

(c)
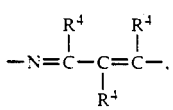

(d)
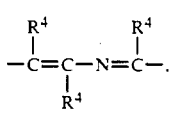

(e)
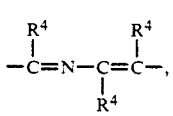

(f)
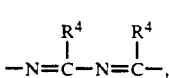

(g)
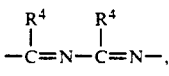

(h)
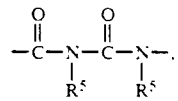

(i)
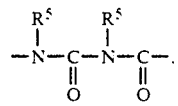

(j)
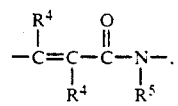

(k)
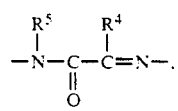

(l)
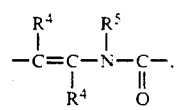

(m)
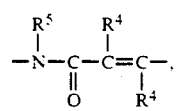

(n)
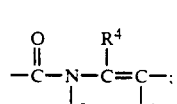

or (o)
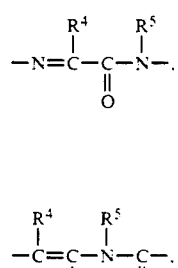

and
E is:
  (a) a single bond,
  (b) —$S(O)_n(CH_2)_s$—, or
  (c) —O—; and
n is 0 to 2; and
s is 0 to 5; and
a is a single bond or absent; and
X is (a) O,
(b) H; H,
(c) H; $CO_2$—$(C_1-C_4)$-alkyl,
(d) H; $CO_2H$,
(e) H; CN,
(f) H; 1H-tetrazol-5-yl, or
(g) H; $CONHSO_2R^{14}$;

$R^2$ is:
(a) H, or
(b) $(C_1-C_6)$-alkyl, and $R^{2a}$ is:
(a) $R^2$,
(b) $CH_2$—aryl
(c) aryl; and $R^4$ groups are independently:
(a) H,
(b) $(C_1-C_6)$-alkyl, $(C_2-C_6)$-alkenyl, or $(C_2-C_6)$-alkynyl, each of which is unsubstituted or substituted with:
  i) OH,
  ii) $(C_1-C_4)$-alkoxy,
  iii) $CO_2R^2$,
  iv) $OCOR^2$,
  v) $CONHR^2$,
  vi) $CON(R^2)_2$,
  vii) $N(R^2)C(=O)R^2$,
  viii) $NH_2$,
  ix) $(C_1-C_4)$-alkylamino,
  x) di[$(C_1-C_4)$-alkyl]amino,
  xi) aryl,
  xii) heteroaryl, wherein heteroaryl is as defined above in $R^1(c)$,
(c) —C(=O)-aryl,
(d) $(C_3-C_7)$-cycloalkyl,
(e) Cl, Br, I, F,
(f) —OH,
(g) —$OR^{21}$,
(h) —$CF_3$,
(i) —SH,
(j) —$S(O)_n$—$(C_1-C_4)$-alkyl,
(k) —$CO_2R^{2a}$,
(l) —$SO_3H$,
(m) —$NR^2R^{21}$,
(n) —$NR^2C(O)R^{21}$,
(o) —$NR^2COOR^{21}$,
(p) —$SO_2NHR^{21}$,
(q) —$SO_2NR^2R^{2a}$,
(r) —$NO_2$,
(s) —$NHSO_2$-$(C_1-C_4)$-alkyl,
(t) —$C(O)NHSO_2R^{14}$,
(u) aryl,
(v) heteroaryl, wherein heteroaryl is as defined above in $R^1(c)$, or
(w) morpholin-4-yl;

$R^5$ is:
(a) H, or
(b) $(C_1-C_6)$-alkyl or $(C_2-C_6)$-alkenyl, unsubstituted or substituted with:
  i) hydroxy, or
  ii) $(C_1-C_4)$-alkoxy; and $R^9$ and $R^{10}$ are each independently:
(a) H,
(b) Cl, Br, I, F,
(c) $NO_2$,
(d) $(C_1-C_6)$-alkyl,
(e) $(C_1-C_6)$-acyloxy,
(f) $(C_3-C_6)$-cycloalkyl,
(g) $(C_1-C_6)$-alkoxy,
(h) —$NHSO_2R^{2a}$,
(i) hydroxy-$(C_1-C_4)$-alkyl,
(j) aryl-$(C_1-C_4)$-alkyl,
(k) $(C_1-C_4)$-alkylthio,
(l) $(C_1-C_4)$-alkylsulfinyl,
(m) $(C_1-C_4)$-alkylsulfonyl,
(n) $NH_2$,
(o) $NH[(C_1-C_4)$-alkyl],
(p) $N[(C_1-C_4)$-alkyl]$_2$,
(q) $CF_3$,
(r) —$SO_2$—$NHR^{2a}$,
(s) furyl, or
(t) aryl, wherein aryl is phenyl or naphthyl unsubstituted or substituted with one or two substituents selected from the group consisting of: Cl, Br, I, F, $(C_1-C_4)$-alkyl, $(C_1-C_4)$-alkoxy, $NO_2$, $CF_3$, $(C_1-C_4)$-alkylthio, OH, $NH_2$, —NH[($C_1-C_4$)-alkyl], —N[($C_1-C_4$)-alkyl]$_2$, —$CO_2H$, or —$CO_2$—$(C_1-C_4)$-alkyl;
(u) when $R^9$ and $R^{10}$ are bonded to adjacent carbon atoms, they can be joined to form an aryl ring;

$R^{11}$ and $R^{12}$ are independently:
(a) H,
(b) Cl, Br, I, F,
(c) $NO_2$,
(d) $NH_2$,
(e) $NH[(C_1-C_4)$-alkyl],
(f) $N[(C_1-C_4)$-alkyl]$_2$,
(g) $SO_2NHR^{2a}$,
(h) $CF_3$,
(i) $(C_1-C_4)$-alkyl,
(j) $(C_1-C_4)$-alkoxy, or
(k) when $R^{11}$ and $R^{12}$ are bonded to adjacent carbon atoms, they can be joined to form an aryl ring;

Z is:
(a) —H,
(b) —$CO_2R^{2a}$,
(c) —$SO_3R^{13}$,
(d) —$NHSO_2CF_3$,
(e) —$PO(OR^{13})_2$,
(f) —$SO_2NHR^{14}$,
(g) —$CONHOR^{13}$,
(h) —$C(R^{2a})(OH)PO(OR^{13})_2$,
(i) —CN,
(j) —$SO_2NH$-heteroaryl, wherein heteroaryl is as defined above in $R^1(c)$,
(k) —$CH_2SO_2NH$-heteroaryl as defined above in $R^1(c)$,
(l) —$SO_2NH$—CO—$R^{14}$,
(m) —$CH_2SO_2NH$—CO—$R^{14}$,
(n) —CONH—$SO_2R^{14}$,
(o) —$CH_2CONH$—$SO_2R^{14}$,
(p) —$NHSO_2NHCO$—$R^{14}$,
(q) —$NHCONHSO_2$—$R^{14}$,
(r) —$NHCO_2R^{2a}$,
(s)

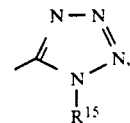

(t)

(u) 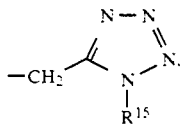

(v) 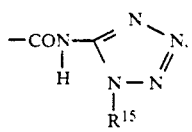

(w) —CONHNHSO$_2$CF$_3$,

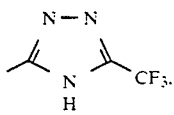

or (x) 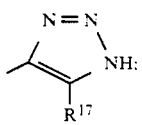

$R^{13}$ is H, or —CHR$^4$—O—C(O)R$^4$;
$R^{14}$ is
 (a) aryl,
 (b) heteroaryl, wherein heteroaryl is as defined above in R$^1$(c),
 (c) (C$_3$-C$_7$)-cycloalkyl,
 (d) (C$_1$-C$_4$)-alkyl unsubstituted or substituted with a substituent selected from the group consisting of aryl, heteroaryl, wherein heteroaryl is as defined above in R$^1$(c), —OH, —SH, (C$_1$-C$_4$)-alkyl, —O(C$_1$-C$_4$)-alkyl, —S(C$_1$-C$_4$)-alkyl, —CF$_3$, Cl, Br, F, I, —NO$_2$, —CO$_2$H, CO$_2$-(C$_1$-C$_4$)-alkyl, —NH$_2$, —NH[(C$_1$-C$_4$)-alkyl]$_2$, —PO$_3$H, PO(OH) (O-(C$_1$-C$_4$)-alkyl);

$R^{15}$ is H, (C$_1$-C$_6$)-alkyl, (C$_2$-C$_4$)-alkenyl, (C$_1$-C$_4$)-alkoxy alkyl, or benzyl, wherein the phenyl is unsubstituted or substituted with a substituent selected from the group consisting of: —NO$_2$, —NH$_2$, —OH or —OCH$_3$;

$R^{17}$ is —CN, —NO$_2$, —CO$_2$R$^{2a}$, or —CF$_3$; and
$R^{21}$ is:
 (a) H, or
 (b) (C$_1$-C$_4$)-alkyl unsubstituted or substituted with:
  i) NH$_2$,
  ii) NH[(C$_1$-C$_4$)-alkyl],
  iii) N[(C$_1$-C$_4$)-alkyl]$_2$,
  iv) CO$_2$H,
  v) CO$_2$(C$_1$-C$_4$)-alkyl,
  vi) OH,
  vii) SO$_3$H, or
  viii) SO$_2$NH$_2$.

The alkyl substitutents recited above denote straight and branched chain hydrocarbons of the length specified such as methyl, ethyl, isopropyl, isobutyl, neopentyl, isopentyl, etc.

The alkenyl an alkynyl substituents denote alkyl groups as described above which are modified so that each contains a carbon to carbon double bond or triple bond, respectively, such as vinyl, allyl and 2-butenyl.

Cycloalkyl denotes rings composed of 3 to 8 methylene groups, each which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The aryl substituent recited above represents phenyl or naphthyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl.

DETAILED DESCRIPTION OF THE INVENTION

GENERAL METHODS FOR PREPARATION OF COMPOUNDS OF GENERAL FORMULA I:

The methods described in PART I AND PART II below illustrate the preparation of angiotensin II antagonists of Formula I. There are several general approaches to the synthesis of antagonists of Formula I, and it is taken as a general principle that one or another method may be more readily applicable for the preparation of a given antagonist; some of the approaches illustrated below may not be readily applicable for the preparation of certain antagonists of Formula I.

It should be recognized that antagonists of Formula I consist of a heterocyclic component designated above by formula I and a benzyl or benzoyl substituted indole or dihydroindole substitutent which is attached to the heterocyclic component through a nitrogen atom. Thus, two generally applicable approaches to antagonists of formula I are these:

1. A heterocycle, designated above as a fused imidazole in Formula I is prepared as described in PART I below. Then the heterocycle is alkylated at a nitrogen atom with N-benzoyl-5-(halomethyl)indole giving the compounds of Formula I. The N-benzoyl-5-(halomethyl)indole is described in Part II below. This alkylating agent is often designated as "Ar—CH$_2$Q where Q is a halide (—Cl,Br,I) or pseudohalide (—OMs, OTs, OTf). In some cases, alkylation may take place at more than one nitrogen atom of the heterocycle, and in these cases, separation by fractional crystallization or by chromotographic methods may be necessary for isolation of the desired product. In some cases, the alkylation step produces a fully-assembled antagonist of Formula I, except that functional groups on the alkylating agent or on the heterocycle may be present in protected form and require deprotection steps to be carried out to complete the synthesis. In most cases, the alkylation is carried out with only a partially assembled indole and requires the alkylation with a substituted benzyl/benzoyl element be carried out in subsequent steps to give the antagonist of Formula I. The alkylation steps and subsequent steps used to prepare antagonists of Formula I, are described in PART II below.

The compounds of this invention maybe resolved using techniques known in the art. The diastereomeric salts or esters of the enantiomers are separated and the desired compound is the more active stereoisomer. The compounds of this invention, their pharmaceutically acceptable salts and their prodrug forms are included within the scope of this invention.

Abbreviations used in the schemes and examples are listed in Table 1.

TABLE 1

| Reagents | |
|---|---|
| NBS | N-bromosuccinimide |
| AIBN | Azo(bis) isobutyronitrile |
| DDQ | Dichlorodicyanoquinone |
| Ac₂O | acetic anhydride |
| TEA | triethylamine |
| DMAP | 4-dimethylaminopyridine |
| PPh₃ | triphenylphosphine |
| TFA | trifluroacetic acid |
| TMS-Cl | trimethylsilyl chloride |
| Im | imidazole |
| AcSK | potassium thioacetate |
| P-TsOH | p-toluenesulfonic acid |
| FMOC-Cl | 9-Fluorenylmethyloxycarbonyl chloride |
| Solvents: | |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| Others: | |
| rt | room temperature |
| TBDMS | t-butyldimethylsilyl |
| OTf | OSO₂CF₃ |
| Ph | phenyl |
| FAB-MS (FSBMS) | Fast atom bombardment mass spectroscopy |
| NOE | Nuclear Overhauser Effect |
| SiO₂ | silica gel |
| trityl | triphenylmethyl |

PART I

Preparation of the 6-fused imidazole heterocycles

BENZIMIDAZOLES

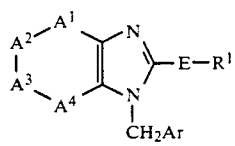

The compounds of Formula I wherein $(-A^1-A^2-A^3-A^4-)$ is a 4-atom sequence as defined in the General Description of the invention can be synthesized using the reactions and techniques described herein below. The reactions are performed in a solvent appropriate to the reagents and materials employed and suitable for the transformation being effected. It is understood by those skilled in the art of organic synthesis that the functionality present on the benzimidazole and other parts of the structure should be consistent with the chemical transformations proposed. Depending upon the reactions and techniques employed, this may involve changing the order of synthetic steps, use of required protecting groups followed by deprotection, and activation of the benzylic position of the alkylating agents used to enable alkylation at the nitrogen on the imidazole part of benzimidazoles.

SCHEME I-1

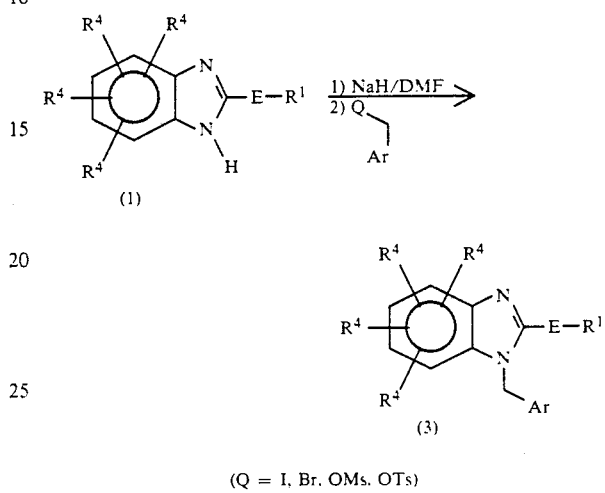

(Q = I, Br, OMs, OTs)

As shown in Reaction Scheme I-1, compounds of Formula (3) can be prepared by carrying out direct alkylation of alkali-metal salt of benzimidazole (1) (preparation of benzimidazoles are described in Schemes I-2 to I-5) using appropriately protected benzyl halide, tosylate (OTs) or mesylate (OMs) derivatives (2). The salt is prepared preferably using MH (where M is lithium, sodium or potassium) in anhydrous dimethylformamide (DMF), or by treating it with metal alkoxide such as sodium or potassium methoxide, ethoxide or t-butoxide in an appropriate alcohol such as methanol, ethanol or t-butanol as the solvent. The alkylation is generally carried-out by dissolving the metal salt of benzimidazole in a dipolar aprotic solvent such as DMF or dimethylsulfoxide (DMSO) and reacting it with the alkylating agent at 20° C. to reflux temperature of the solvent for 1-24 hours.

If substituents on the benzene ring result in an unsymmetrical benzimidazole, the alkylation may produce a mixture of two regioisomers as products. These regioisomers possess distinct physico-chemical and biological properties and in most cases can be separated and purified by using conventional separation techniques such as chromatography (flash column chromatography, medium-pressure liquid chromatography, high pressure liquid chromatography (HPLC) and/or crystallization. In those cases where separation of regioisomers is difficult by conventional techniques, the mixture can be transformed into suitable derivatives that can be separated by usual separation methods. The structural assignments of the isomers can be made using proton NMR, Nuclear Overhauser Effect (NOE) experiments or X-ray crystallography.

REACTION SCHEME I-2

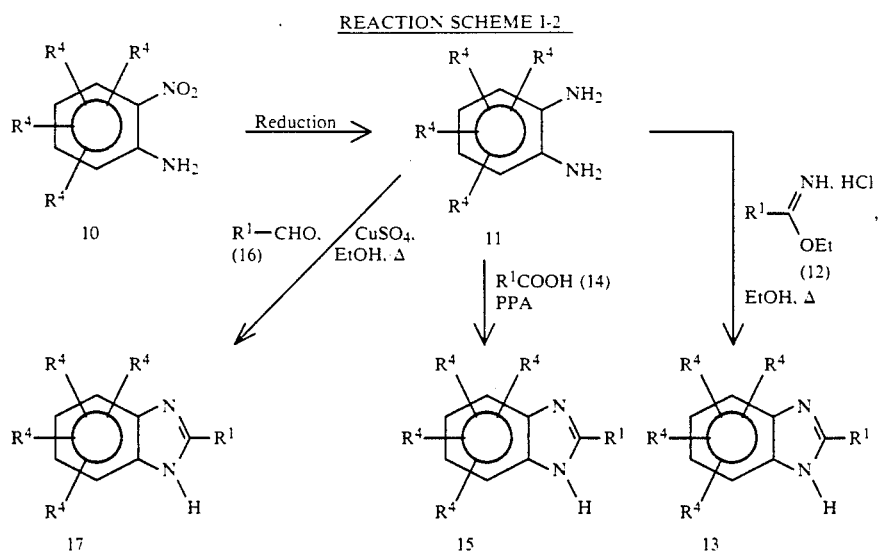

The starting benzimidazoles can be readily prepared by any of the standard procedures described in the litrature [P. N. Preston, *Chemistry of Heterocyclic Compounds*. Vol. 40, part I, pp. 1-286 (1981) and references cited therein]. Several alternative routes to obtain benzimidazoles are outlined in Scheme I-2. The most widely used starting material, o-phenylenediamines (11), can be readily prepared from the corresponding o-nitroaniline (10) using standard reductive procedures such as metal-acid reduction or catalytic reduction. The substituted or unsubstituted (11) can then be treated with an appropriate imidate hydrochloride (12) to form corresponding benzimidazoles (13). Alternatively, the reaction of carboxylic acids (14) with o-phenylenediamines in the presence of polyphosphoric acid (PPA) is also effective in producing benzimidazoles (15). Benzimidazoles (17) can also be prepared from o-phenylenediamines and aldehyde (16) using cupric salt as an oxidant [R. Weidenhagen, *Chem. Ber.*, 69, 2263 (1936)].

SCHEME I-10

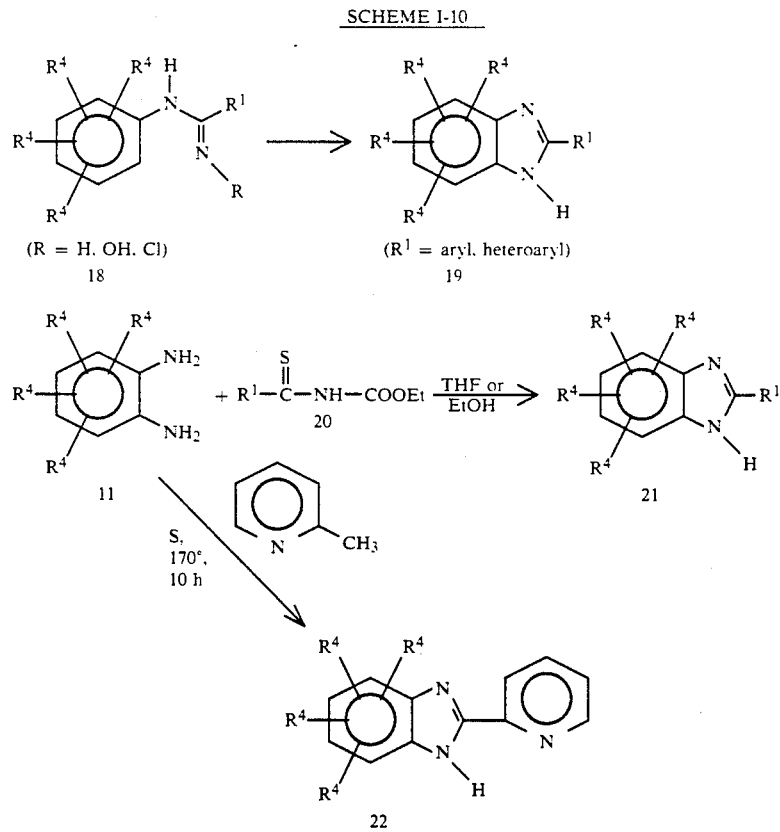

Although some benzimidazoles having aryl and heteroaryl groups at the 2 position can be prepared using the methods described in Reaction Scheme I-2, Scheme I-3 outlines methods which are more suitable for the synthesis of this class of compounds. N'-aryl-N-hydroxyamidines (18; R=OH) are cyclized under mild conditions using benzene-sulfonyl chloride in pyridine or triethylamine to give 19 in good yield [M. W. Partridge and H. A. Turner, *J. Chem. Soc.*, 2086 (1958)]. Parent amidines (18; R=H) can also be oxidized with sodium hypochlorite under basic conditions to form 19 [V. J. Grenda, R. E. Jones, G. Gal and M. Sletzinger, *J. Org. Chem.*, 30, 259, (1965)].

Alternatively, as shown in Reaction Scheme I-3, o-phenylenediamines (11) can be reacted with N-ethoxycarbonylthioamides (20) to give 2-substituted benzimidazoles (21) in excellent yields. This method avoids the use of acidic catalysts. The reagents (20) are easily obtained in one step from ethoxycarbonyl isothiocyanate and simple aromatic or heterocyclic compounds or alkylmagnesium halides [B. George and E. P. Papadopoulos., *J. Org. Chem.*, 41, 3233(1976); E. P. Papadopoulos., *J. Org. Chem.*, 41, 962(1976)]. Heterocyclic compounds containing reactive methyl groups (e.g., 2-picoline) can also be reacted with o-phenylenediamines in the presence of sulfur at elevated temperatures to give 2-heteroaryl benzimidazoles (22).

29) can be prepared from the corresponding benzimidazolones (25) or benzimidazolethiones (28). Benzimidazolones are conveniently prepared from o-phenylenediamines and phosgene or urea [K. Hofmann, "Imidazole and its Derivatives, Part 1," Wiley-Interscience, New York, 1953, pp. 285-291]. Carbonate esters, diethylpyrocarbonate, N,N-carbonyldiimidazole and N,N-diethylcarbamyl chloride may also be used in this reaction. The reaction of phosgene is apparently facilitated by the use of N,N'-bis-trimethylsilyl (TMS) derivative (23) instead of the parent diamine [L. Birkhofer, H. P. Kuhlthau, and A. Ritter, *Chem. Ber.*, 93, 2810 (1960)].

REACTION SCHEME I-5

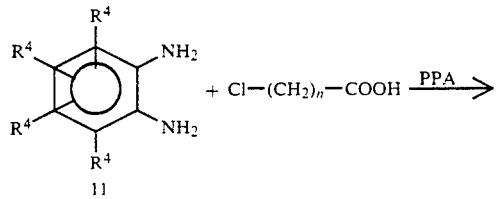

SCHEME I-4

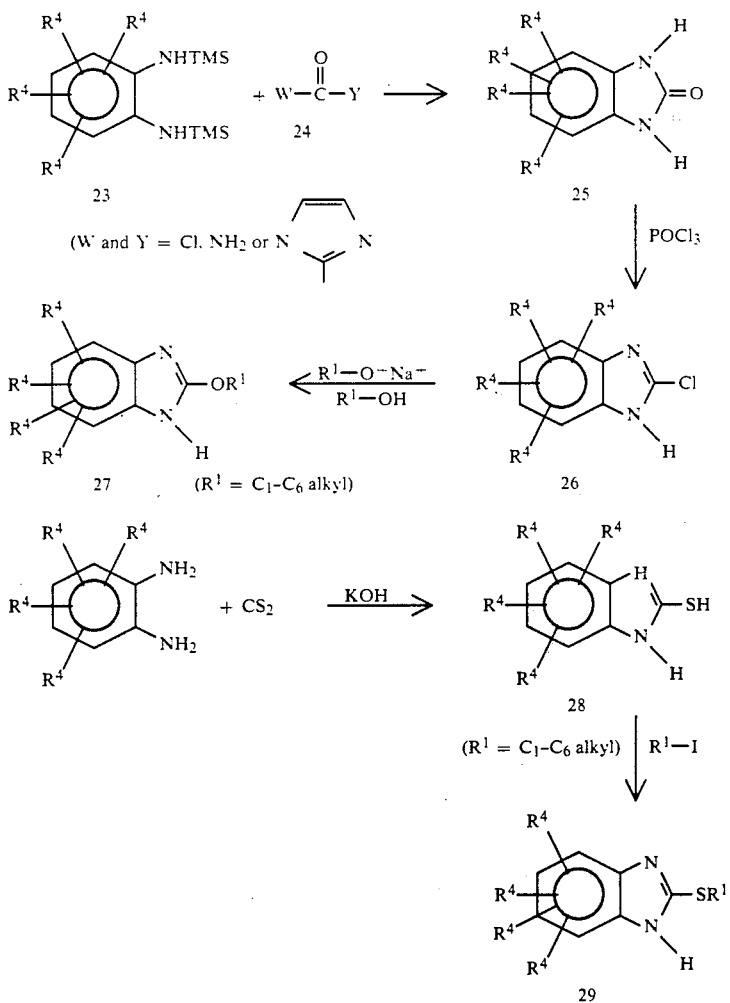

As outlined in Reaction Scheme I-4, benzimidazoles containing 2-alkoxy and thioalkyl substituents (27 and -continued
REACTION SCHEME I-5

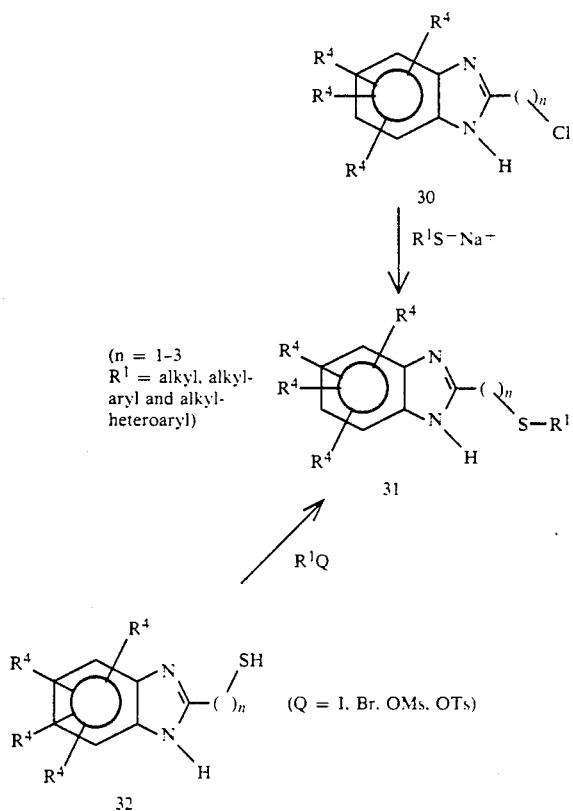

(n = 1-3
$R^1$ = alkyl, alkylaryl and alkylheteroaryl)

(Q = I, Br, OMs, OTs)

As described in Reaction Scheme I-5, 2-alkylthioalkyl substituted benzimidazoles (31) can be prepared from the reaction of RS-M (where M is sodium, potassium or lithium) with 2-chloroalkyl benzimidazoles (30). 2-Chloroalkyl benzimidazoles (30) can be conveniently prepared from the diamines and the chloroalkyl carboxylic acids using PPA [W. Knobloch, *Chem. Ber.*, 91, 2557 (1958)]. Alternatively, compound 31 can also be prepared from the readily available 2-thioalkyl derivative (32) [E. S. Milner, S. Snyder, and M.M. Joullie, *J. Chem. Soc.*, 4151 (1964)].

IMIDAZO-6-FUSED HETEROCYCLES

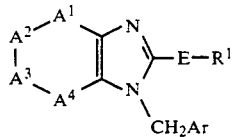

The compounds of Formula I, can be synthesized using the reactions and techniques described herein below. The reactions are preformed in a solvent appropriate to the reagents and materials employed and suitable for the transformation being effected. It is understood by those skilled in the art of organic synthesis that the functionality present on the heterocycle and in the reactants being employed should be consistent with the chemical transformations being conducted. Depending upon the reactions and techniques employed, optimal yields may require changing the order of synthetic steps or use of protecting groups followed by deprotection.

As shown in Reaction Scheme II, compounds of Formula I can be prepared by carrying-out direct alkylation of alkali-metal salts of heterocycles (1) using appropriately protected benzyl halide, tosylate (OTs) or mesylate (OMs) derivatives (2). The salt is prepared preferably using MH (where M is lithium, sodium or potassium) in anhydrous dimethylformamide (DMF), or by treating it with a metal alkoxide such as sodium or potassium methoxide, ethoxide or t-butoxide in an appropriate alcohol such as methanol, ethanol or t-butanol as the solvent. The alkylation is generally carried-out by dissolving the metal salt of the heterocycle in a dipolar aprotic solvent such as DMF or dimethylsulfoxide (DMSO) and reacting it with the alkylating agent at 20° C. to reflux temperature of the solvent for 1-24 hours.

If substituents and/or the hetero atom positions in the six membered ring are not symmetrically disposed, the alkylation on the imidazole nitrogen(s) generally produces a mixture of two regioisomers as products arising from $N^1$ and $N^3$ alkylation. These regioisomers I and Ia possess distinct physico-chemical and biological properties and in most cases can be separated and purified by using conventional separation techniques such as chromatography (flash column chromatography, medium-pressure liquid chromatography, high performance liquid chromatography) and/or crystallization. In those cases where separation of regioisomers is difficult by conventional techniques, the mixture can be transformed into suitable derivatives that can be separated by the above separation methods. The structural assignments of the isomers can be made using Nuclear Overhauser Effect (NOE), $^1H$-$^{13}C$ coupled NMR experiments or X-ray crystallography.

When there is potential for alkylation of the 6-membered heterocyclic ring, this can be avoided by the use of suitable protecting groups.

The heterocycles of type (1) can be prepared by any of the standard procedures described in the literature [J. A. Montgomery and J. A. Secrist III in "Comprehensive Heterocyclic Chemistry," Vol. 5, A. R. Katritsky and C. W. Rees Eds., Pergamon Press 1984; pp 567-597 and 631-656 and references cited therein]. As shown in Reaction Scheme I-6, the most widely used starting materials are six member heterocyclic vicinal diamines (9). Fused imidazoles (10) can be prepared by condensation of (9) with an appropriate carboxylic acid, nitrile, imidate ester, or orthoester, either neat, or in a solvent appropriate and compatible with the starting materials and reagents, such as polyphosphoric acid, ethanol, methanol, hydrocarbon solvents, and with a catalytic amount of acid if required. Oxidation of an imine formed by reaction of diamine (9) with an appropriate aldehyde using oxidants such as Cu (II), nitrobenzene, or 2,3-dichloro-5,6-dicyano-1,4-benzoquinone (DDQ) also affords heterocycles (10). Aminoamides (11, W=H) or diamides (11, W=$R^6$CO) can be converted to fused imidazoles (10) by heating neat, or at an elevated temperature in a solvent such as xylene under acidic or neutral conditions.

As shown in Reaction Scheme I-17, methods of preparing heterocycles of types (12 and 13) involve treatment of diamines (9) with reagents such as urea, phosgene, potassium cyanate, alkyl chloroformates, dialkylcarbonate, or carbon disulfide in the presence of bases such as potassium hydroxide or potassium carbonate. Amino acids (14) or (15) can be converted to (13) via Curtius or Hoffman rearrangement on suitable derivatives such as acyl azides, hydroxyamides, or N-haloamides. Bicyclic compounds of type (16, E=sulfur or oxygen) are formed from 12 by reaction under neutral or basic conditions with alkyl halides, alkylmesylates, alkyltosylates, trialkyloxonium salts, or with an appropriate diazoalkane. Compounds of type (16; E=oxygen or sulfur) are prepared by displacement reactions using alkoxides or alkyl mecaptides with chloro intermediates as indicated.

Diamines of type 9 can be prepared by a wide variety of methods such as hydrolysis of bis-amides or amino amides, reduction of dinitro or aminonitro or hydrazino or azido groups, displacement of heteroaromatic halides or alkoxy or thio or alkylthio or hydroxy or alkyl sulfonyl groups with ammonia or amines, or rearrangement of acyl azides or amides or acids (Curtius, Hoffman, or Schmidt rearrangements). [A. S. Tomcufcik, L. N. Starker in "Heterocyclic Compounds, Pyridine and it's Derivatives" Pt 3, E. Klingsberg Ed., Wiley Interscience, 1962, pp 59-62, and references cited there in; T. Nakagome in "Heterocyclic Compounds, Pyridazines" Vol. 28, R. N. Castle, Ed., Wiley Interscience, 1973, pp 597-601, and references cited therein; "Heterocyclic Compounds, The Pyrimidines" Vol. 16, D. J. Brown Ed., Wiley Interscience 1985, pp 299-325; E. Schipper, and A. R. Day J. Am. Chem. Soc. (1952) 74, 350; "Comprehensive Heterocyclic Chemistry," Vol. 5, A. R. Katritsky and C. W. Rees Eds., Pergamon Press 1984; pp 567-597 and 631-656 and references cited therein].

In cases wherein heterocycles of type 10 or 16 are not easily prepared from their corresponding diamines, or when these diamines cannot be prepared then alternative routes, involving fusion of the six member heterocycle onto an appropriately substituted imidazole, are used. Two of these routes are illustrated in Reaction Scheme I-8. For example, imidazo[4,5-d][1,2,3]triazines (18) are preferentially prepared by treatment of amino carboxamido imidazoles (17) with sodium nitrite in aqueous acid. Precursor imidazoles (17) are prepared by degradation of an appropriately substituted xanthine or by condensation of an appropriate imidate ester with aminocyanoacetamide. Imidazo[4,5-b]-pyridazines (20) can be prepared from imidazodicarboxylate esters (19) by treatment with hydrazine. Oxidation of (20) gives pyridazindiones (21). The oxygen(s) in (20) or (21) can be converted to other functionalities such as halides or thiones, which are themselves precursors for the synthesis of more elaborate systems ["Comprehensive Heterocyclic Chemistry," Vol. 5, A. R. Katritsky and C. W. Rees Eds., Pergamon Press 1984; pp 567-597 and 631-656 and references cited therein].

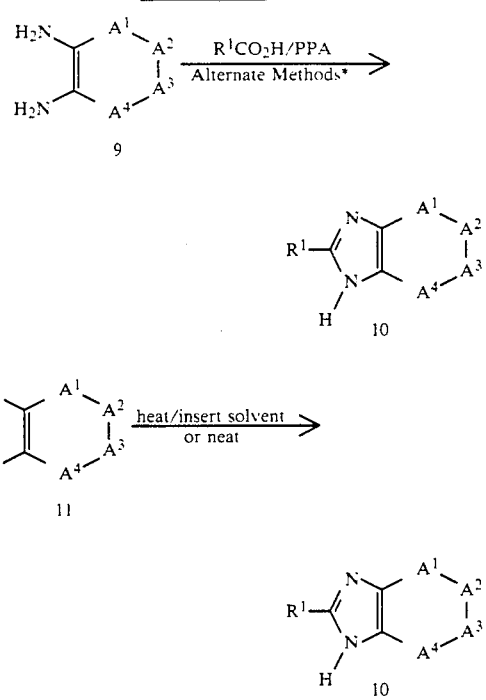

SCHEME 1-6

*Alternate reagents and reaction conditions:
$R^1$—CN, PPA
$R^1$—C(=NH·HCl)(OC$_2$H$_5$), C$_2$H$_5$OH, $\Delta$
$R^1$C(OCH$_3$)$_3$, toluene, H$^-$, $\Delta$
$R^1$CHO, C$_2$H$_5$OH, Cu(OCH$_3$)$_2$

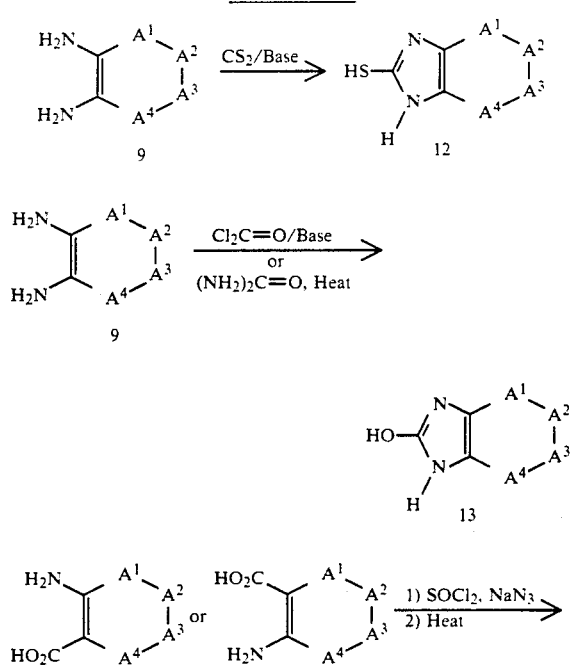

SCHEME 1-7

-continued
SCHEME I-7

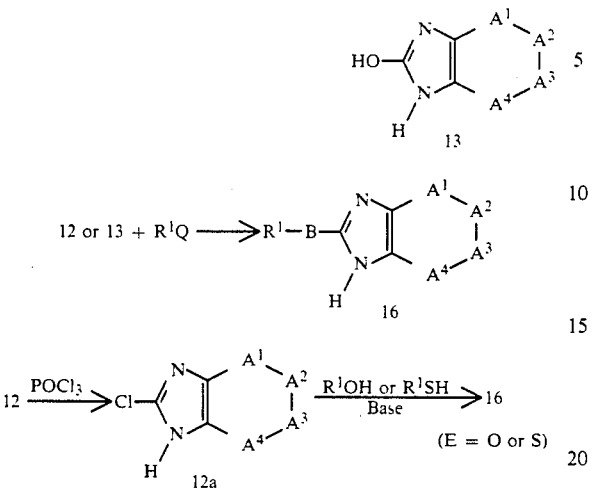

(E = O or S)

SCHEME I-8

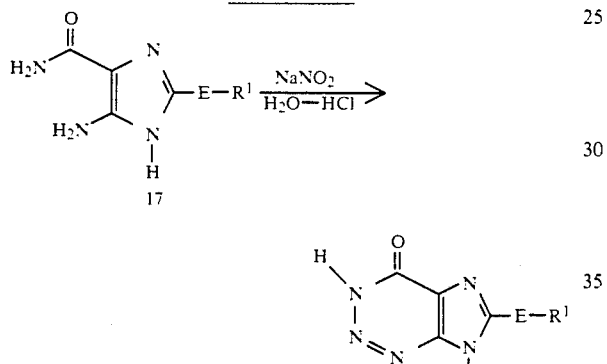

-continued
SCHEME I-8

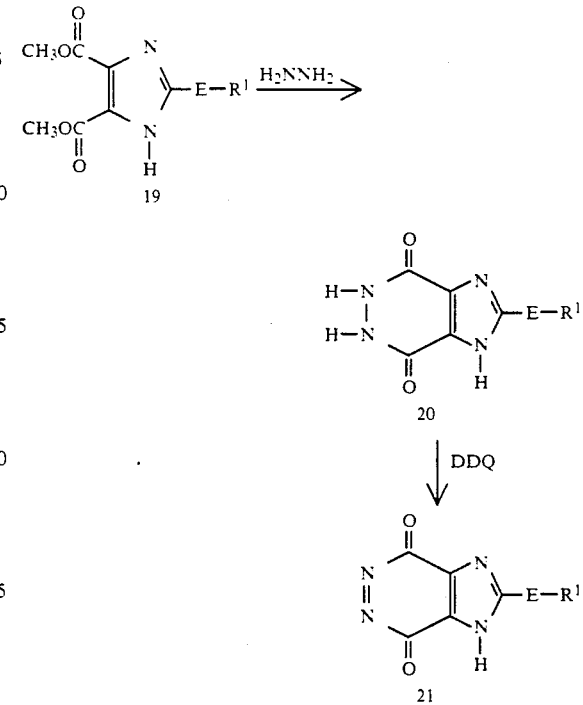

Moreover as shown in Scheme I-9 amino imidazole esters and amides are versatile intermediates for the preparation of purines. This scheme also illustrates the synthesis of the 6-membered heterocyclic ring after the alkylating agent 2 has been reacted with a suitably substituted imidazole to afford 22 or 24.

SCHEME I-9

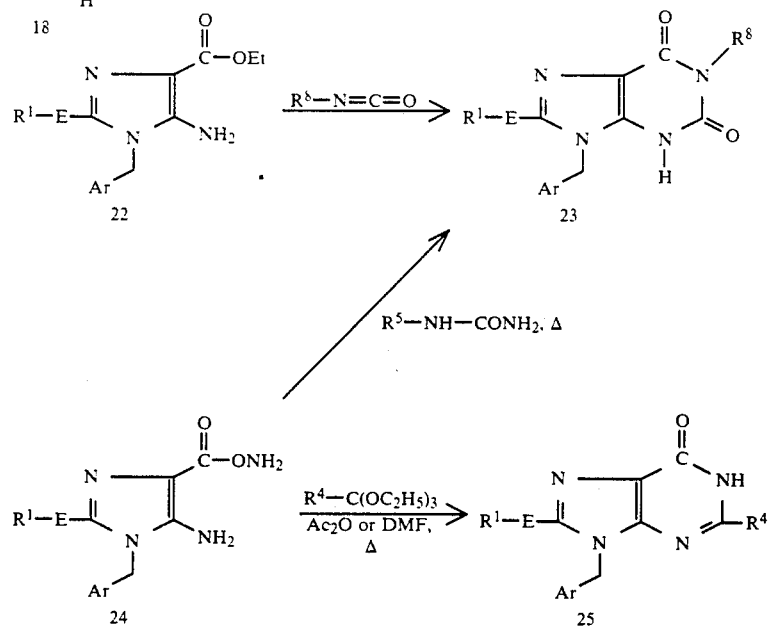

The preparation of reduced forms of heterocycles can be achieved by catalytic reduction, or by synthesis from a suitable imidazole precursor. For example, histidine and derivatives thereof react with formaldehyde to afford partially saturated imidazo[4,5-c] pyridines [cf. Neuberger, A. Biochem. J., (1944), 38, 309].

PART II

Preparation of indole containing analogs and alkylation with the heterocycles described in Part I.

The 5-methylindole 1a is benzoylated with benzyl chloride of a substituted benzoic acid to give N-benzoyl-5-methylindole, 1b. The bromination of 1b with N-bromosuccinimide and a catalytic amount of azobisisobutyronitrile in refluxing carbon tetrachloride affords N-benzoyl-5-bromomethylindole, 1c.

SCHEME II-1

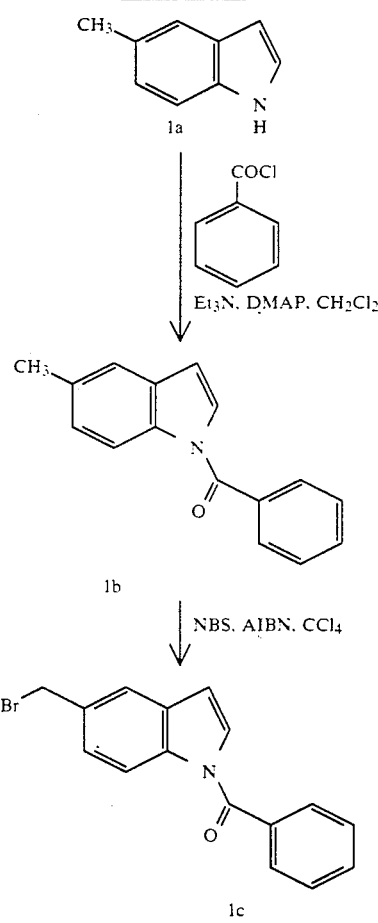

The heterocycle for example, imidazopyridine 2a can be alkylated by deprotonation with sodium hydride and dimethylformamide to give the sodium salt 2b which is alkylated with the N-benzoyl-5-bromomethyl indole, 1c to afford 2c.

SCHEME II-2

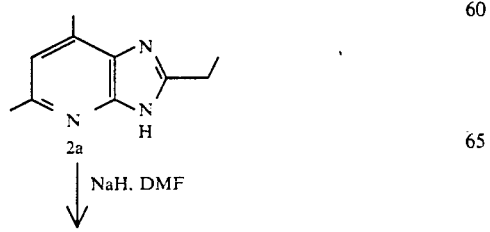

-continued
SCHEME II-2

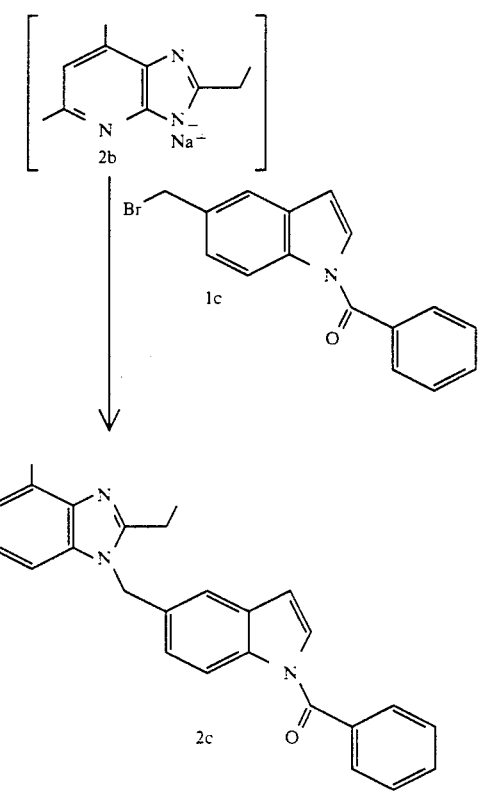

SCHEME II-3

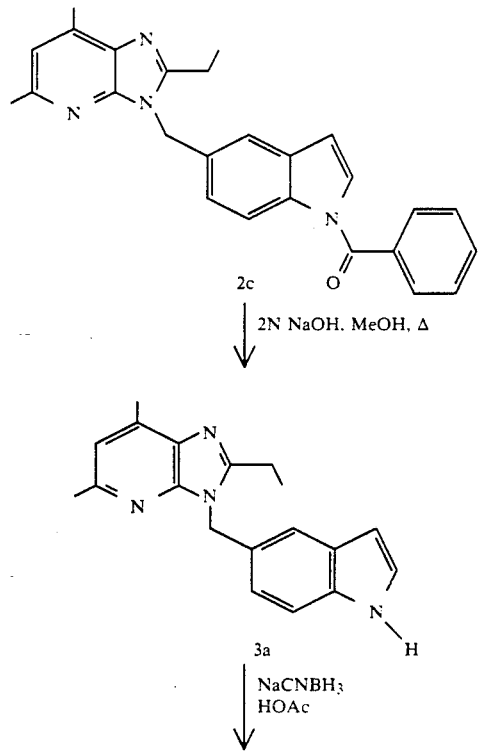

-continued

SCHEME II-3

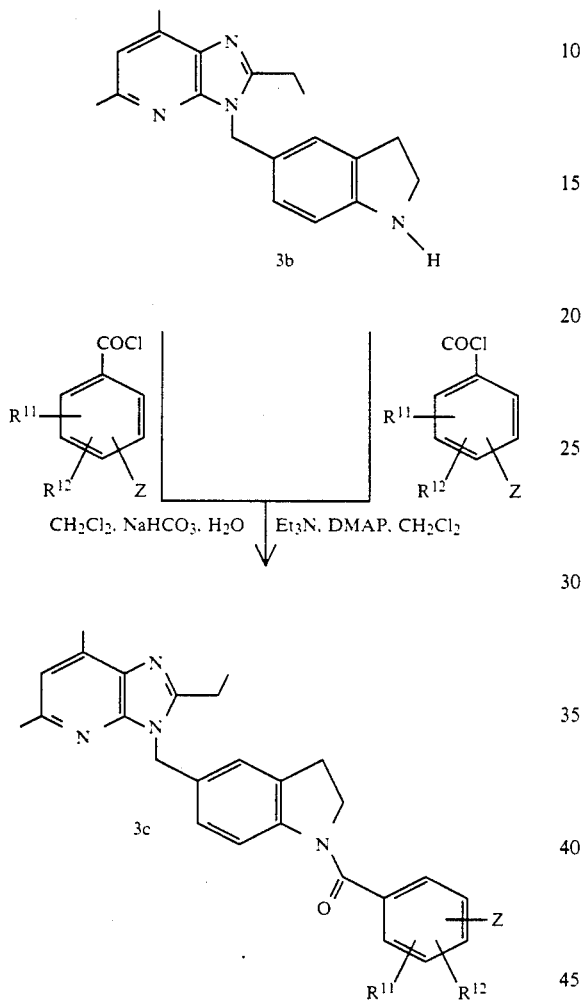

The dihydroindole analog, 3c is prepared by first hydrolyzing the N-benzoyl group of 2c with 4N sodium hydroxide to give the indole 3a. Treatment of the indole 3a with sodium cyanoborohydride and acetic acid gives the dihydroindole analog 3b. The dihydroindole analog 3b can be acylated using one of two possible routes both of which use the substituted benzoyl chloride: 1) aqueous solution of sodium bicarbonate, dichloromethane or 2) triethylamine, dimethylaminopyridine in dichloromethane to give the acylated dihydroindole 3c.

The tetrazole containing analogs 4a are prepared by treatment of the nitrile 2c or 3c with azido trimethylstannane in toluene at reflux.

SCHEME II-4

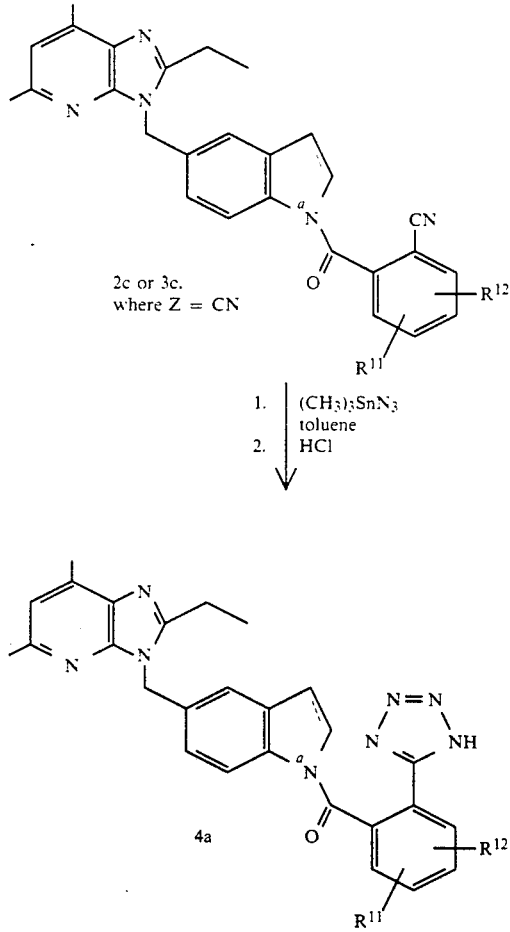

The indole derivative 3a is acylated either with acid anhydrides or acid chlorides in the presence of NaH in dimethylformamide to afford 5a or 5b.

SCHEME II-15
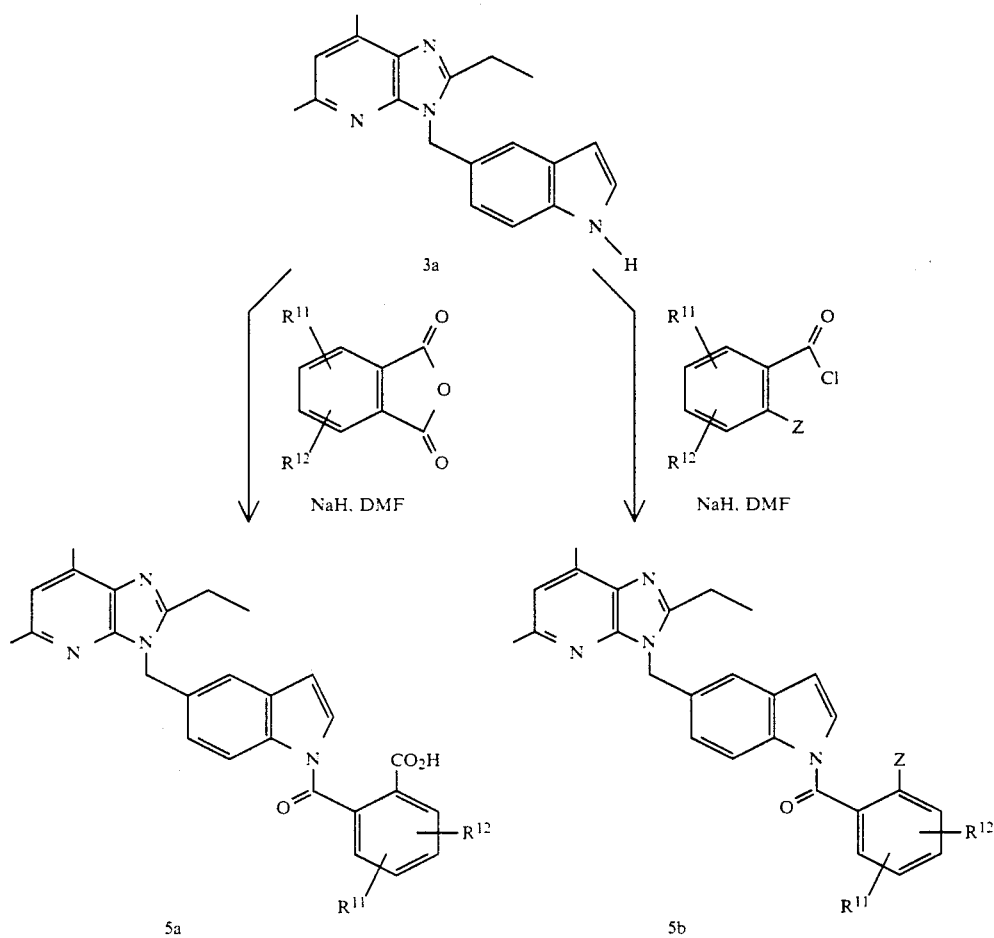
Treatment of the indole derivative, 3a with NaH in dimethylformamide, followed by treatment with isatoic anhydride affords the carbamic acid 6.
SCHEME II-6
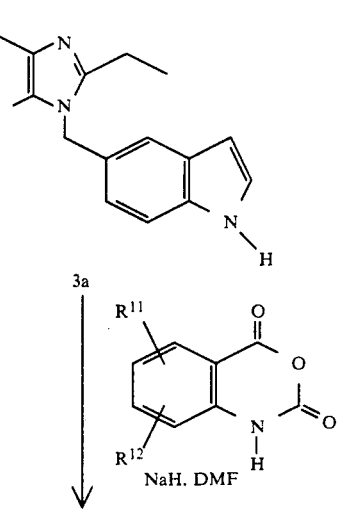
-continued
SCHEME II-6
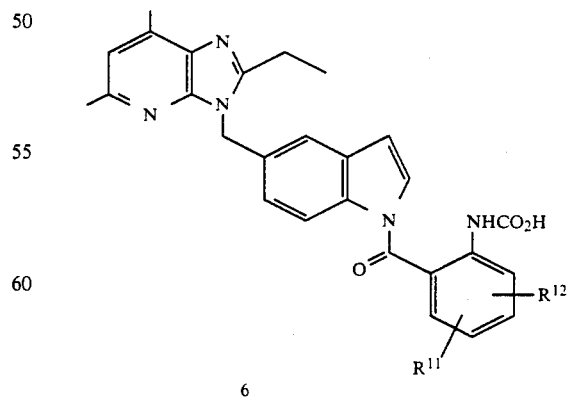
Treatment of the dihydroindole 3b with various aldehydes under Strecker conditions produces the cyano compound 7.

SCHEME II-7

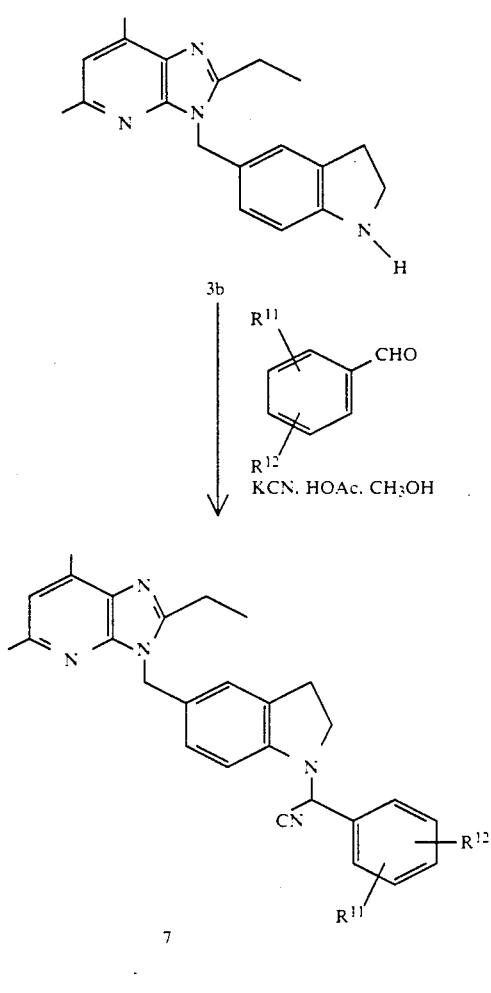

SCHEME II-8

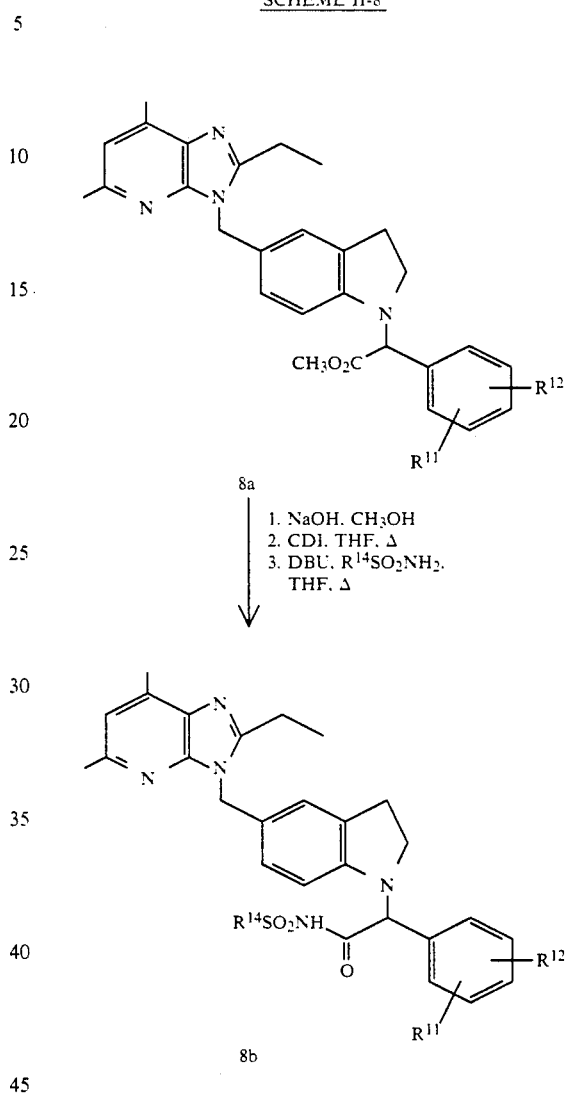

SCHEME II-8

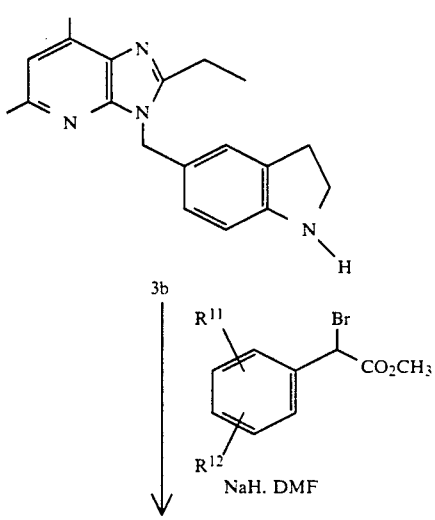

Alkylation of the dihydroindole 3b with various substituted methyl α-bromophenylacetates in the presence of NaH in dimethylforamide affords the substituted indole, 8a. Saponification of 8a with aqueous sodium hydroxide in methanol gives the acid. Treatment of the acid with carbonyl diimidazole in tetrahydrofuran gives the acylimidazole, which upon reflux in a THF solution of diazabicycloundeccane and the appropriate sulfonamde gives the acylsulfonamide, 8b.

Alkylation of the indole 3a with various aryl bromides in the presence of NaH in dimethylformamide gives the substituted N-benzoylindole compound 9.

SCHEME II-9

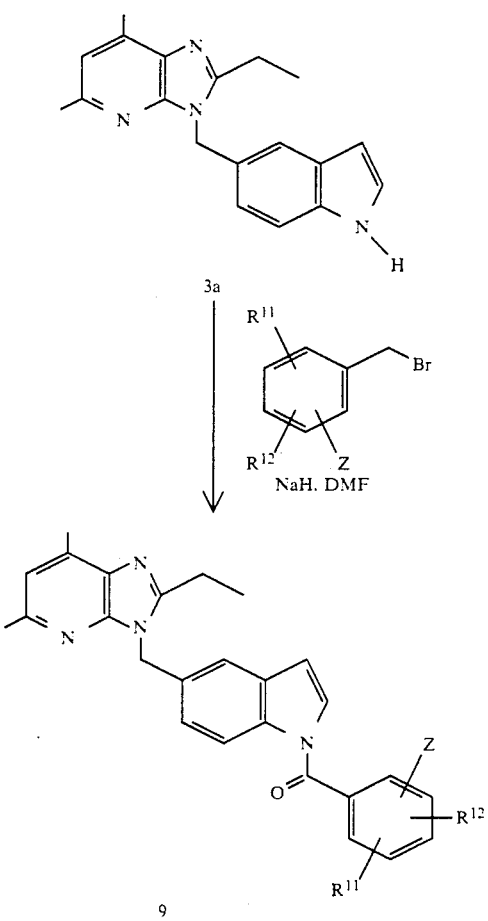

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methanesulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor binding assay using rabbit aortae membrane preparation

Three frozen rabbit aortae (obtained from Pel-Freeze Biologicals) were suspended in 5 mM Tris-0.25M Sucrose, pH 7.4 buffer (50 ml) homogenized, and then centifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitration and the suspension was used for 100 assay tubes. Samples tested for screening were done in duplicate. To the membrane preparation (0.25 ml) there was added $^{125}$I-Sar$^1$Ile$^8$-angiotensin II [obtained from New England Nuclear] (10 μl; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^{125}$I-Sar$^1$Ile$^8$-angiotensin II was presented as a measure of the efficacy of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris. HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF) (0.1 mM)]. (For screening of compounds, generally duplicates of tubes are used). To the membrane preparation (0.5 ml) there was added 3H-angiotensin II (50 mM) (10 μl) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^3$H-angiotensin II was presented as a measure of the efficacy of such compounds as AII antagonists.

Using the methodology described above, representative compounds of the invention were evaluated and were found to exhibit an activity of at least $IC_{50} < 50$ µM thereby demonstrating and confirming the utility of the compounds of the invention as effective AII antagonists.

The potential antihypertensive effects of the compounds described in the present invention may be evaluated using the methodology described below:

Male Charles River Sprague-Dawley rats (300-375 gm) were anesthetized with methohexital (Brevital: 50 mg/kg i.p.). The trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volumn—1.1 cc per 100 grams body weight). The right carotid artery was ligated, both left and right vagal nerves were cut, the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered and 15 minutes later propranolol (1 mg/kg i.v.). Thirty minutes later antagonists of formula I were administered intravenously or orally. Angiotensin II was then typically given at 5, 10, 15, 30, 45 and 60 minute intervals and every half-hour thereafter for as long as the test compound showed activity. The change in the mean arterial blood pressure was recorded for each angiotensin II challenge and the percent inhibition of the angiotensin II response was calculated.

Thus, the compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinapathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Perferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, *rauwolfia serpentina*, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of Formula I and their incorporation into pharmaceutical compositions and as such are not to be considered nor construed as limiting the invention set forth in the claims appened hereto.

EXAMPLE 1

3-(N-Benzoyl-5-indolyl)methyl-5,7-dimethyl-2-ethyl-3H-imidazo[4,5-b]pyridine

Step A: Preparation of 2-nitramino-4,6-dimethylpyridine

2-Amino-4,6-dimethylpyridine (10.0 g, 81.8 mmol) was added portion-wise to 65 mL of $H_2SO_4$ (conc. d=1.84) which was stirred (mechanical) at 0° C. After complete addition, the mixture was warmed to room temperature until the mixture became homogeneous. The solution was then cooled to $-10°$ C. and a pre-cooled (0° C.) mixture of conc $HNO_3$ (11.5 mL, d=1.40) and $H_2SO_4$ (8.2 mL, d=1.84) was added at such a rate as not to raise the internal reaction temperature above $-9°$ C. Ten minutes after the addition was complete this cooled ($-10°$ C.) mixture was poured onto 400 g of crushed ice. The resulting slurry was neutralized by the addition of conc $NH_4OH$ (to pH 5.5) while cooling (ice bath). The solid was isolated by filtration, and dried at room temperature to give 13.3 g of the title compound as a white solid.

Step B: Preparation of 2-amino-3-nitro-4,6-dimethylpyridine

To 75 mL of stirred conc $H_2SO_4$ cooled to $-5°$ C. (ice-salt bath) was added 4,6-dimethyl-2-nitraminopyridine (13.2 g, 79 mmol) portion-wise at such a rate as to maintain the internal temperature below $-3°$ C. The mixture was warmed to 0° C. until homogeneous (30 minutes) at which time tlc ($SiO_2$, 1:1 EtOAc/hexanes on a $NH_4OH$ neutralized aliquot) indicated that the rearrangement was complete. The mixture was poured onto 400 g of crushed ice and the pH was adjusted to 5.5 by the addition of conc $NH_4OH$. The resulting yellow slurry was cooled to 0° C., filtered, washed with cold water (50 mL), and dried at room temperature to give 10.32 g of a mixture of the title compound and the 5-nitro isomer in a 55:45 ratio (determined by $^1H$ NMR). This mixture was used directly in the next step.

Step C: Preparation of 5,7-dimethyl-2-ethylimidazo[4,5-b]pyridine

To a mixture of 8.44 g of a 55:45 mixture of 2-amino-3-nitro-4,6-dimethylpyridine and 2-amino-5-nitro-4,6-dimethylpyridine in MeOH (1.2 L) was added 10% Pd/C (2.4 g). The reaction vessel was evacuated then purged with $H_2$ at 1 atm. and stirred vigorously for 18 h. Filtration through a celite pad, and concentration gave 6.65 g of a mixture of 2,3-diamino-4,6-dimethylpyridine and 2,5-diamino-4,6-dimethylpyridine as a dark solid. To 5.40 g (39.4 mmol) of this mixture was added propionic acid (8.80 mL, 118 mmol) followed by polyphosphoric acid (100 mL). This stirred mixture was heated to 90° C. for 3 h then to 100° C. for 1 hour. The inside walls of the flask were scraped with a spatula to assist dissolution of the solids. After the reaction was complete, the warm mixture was poured onto 300 g of ice and the mixture was made basic with $NH_4OH$. The mixture was extracted (4×50 mL $CH_2Cl_2$), dried ($K_2CO_3$) and concentrated to give a mixture of the title compound and 4,6-dimethyl-2,5-bis(propionamido)pyridine. Purification ($SiO_2$, 5% MeOH/EtOAc) gave 1.66 g of the titled compound as the slower eluting component.

$^1H$ NMR ($CD_3OD$, 300 MHz, ppm): δ6.95 (s, 1H), 2.92 (q, J=7.8 Hz, 2H), 2.54 (apparent s, 6H), 1.40 (t, J=7.8 Hz, 3H).

Step D: Preparation of N-benzoyl-5-methylindole

To a solution of 5-methylindole (1.0 g, 7.6 mmol) in 8.0 mL of $CH_2Cl_2$ was added N,N-dimethylamino pyridine (0.186 g, 1.52 mmol), 2.12 mL (15.24 mmol) of triethylamine and 0.97 mL (1.18 g, 8.39 mmol) of benzoyl chloride. The resulting solution was stirred for 16 hours at room temperature. The solution was diluted with 500 mL of $CH_2Cl_2$ and washed with 200 mL of saturated aqueous $NaHCO_3$ and 200 mL of brine. The organic phase was dried over $MgSO_4$, filtered, and concentrated to a yellow oil. The resultant oil was flash chromatographed eluting with 20% ethyl acetate in hexane yielding 1.73 g (96%) of the titled compound as a white powder.

FAB-MS: m/e=236 (M+1).

$^1H$ NMR (300 MHz, $CDCl_3$, ppm) d 8.29 (d, 1H); 7.71 (d, 2H); 7.56 (d, 1H); 7.51 (d, 2H); 7.38 (s, 1H); 7.24 (d, 1H); 7.20 (d, 1H); 6.53 (d, 2H); 2.47 (s, 3H).

Step E: Preparation of N-benzoyl-5-(bromomethyl)-indole

A suspension of the product of Step A (5.5 g, 23.4 mmol) in 10 mL of $CCl_4$ was heated to reflux. N-bromosuccinimide (4.6 g, 25.7 mmol) and several crystals (approximately 100 mg) of azoisobutyronitrile (AIBN) were added. The resultant solution was stirred at reflux for 4 hours. The solution was cooled, diluted with 1.5 L of $CH_2Cl_2$ and washed with 400 mL of $H_2O$ and 400 mL of brine. The organic phase was dried over $MgSO_4$, filtered and concentrated to a brown oil. The resultant oil was flash chromatographed eluting with 10:1 hexane/ethyl acetate to afford the titled compound (5.6 g, 80%) as a yellow powder.

FAB-MS: m/e=314 (M+1).

$^1$H NMR (300 MHz, CDCl$_3$, ppm) d 8.35 (d, 1H); 7.73 (d, 2H); 7.63 (s, 1H); 7.61 (d, 1H); 7.55 (d, 2H); 7.41 (d, 1H); 7.33 (d, 1H); 7.33 (d, 1H); 6.60 (d, 1H); 4.66 (s, 2H).

Step F: Preparation of 3-(N-Benzoyl-5-indolyl)methyl-5,7-dimethyl-2-ethyl-3H-imidazo[4,5-b]pyridine To a solution of 5,7-dimethyl-2-ethylimidazo[4,5-b]pyridine of Step C (1 g, 5.7 mmol) in 10 mL of DMF was added 251 mg (6.29 mmol, 1.1 eq) of 60% NaH. After 5 minutes the evolution of hydrogen had ceased and 2.33 g (7.43 mmol, 1.3 eq) of Step E was added. The mixture was stirred for 2.5 hours and the DMF removed in vacuo. The resultant brown oil was flash chromatographed with 2:1 ethyl acetate/hexane to yield 1.74 g (75%) of the titled compound as a tan oil which crystallized on standing.

FAB-MS: m/e=409 (M+1).

$^1$H NMR (300 MHz, CDCl$_3$, ppm) d 8.31 (d, 1H); 7.70 (d, 2H); 7.58 (d, 1H); 7.52 (d, 2H); 7.28 (s, 1H); 7.26 (s, 1H); 7.22 (d, 1H); 6.90 (s, 1H); 6.49 (d, 1H); 5.59 (s, 2H); 2.80 (q, 2H); 2.65 (s, 3H); 2.61 (s, 3H); 1.30 (t, 3H).

EXAMPLE 2

Preparation of 3-[N-(2-carboxybenzoyl)-5-indolyl]methyl-5,7dimethyl-2-ethyl-3H-imidazo[4,5-b]pyridine Step A: Preparation of 3-(5-indolyl)methyl-5,7-dimethyl-2-ethyl-3H-imidazo[4,5-b]pyridine To a suspension of the product of Example 1 (500 mg, 1.225 mmol) in 10 ml of methanol was added 10 ml of 2N NaOH and the mixture heated to 60° C. After 18 hours the methanol was removed in vacuo. The reaction mixture was diluted with 150 mL of H$_2$O and extracted with 3×200 mL of CH$_2$Cl$_2$. The combined extracts were dried over Na$_2$SO$_4$, filtered and concentrated to yield by the titled compound (377 mg, 100%) as a pale yellow powder.

FAB-MS: m/e=305 (M+1).

$^1$H NMR (300 MHz, CD$_3$OD, ppm) d 7.34 (d, 1H); 7.31 (s, 1H); 7.22 d, 1H); 7.01 (s, 1H); 6.94 (d, 1H); 6.39 (d, 1H); 5.61 (s, 2H); 2.87 (q, 2H); 2.63 (s, 6H); 1.24 (t, 3H).

Step B: Preparation of 3-[N-(2-carboxybenzoyl)-5-indolyl]methyl-5,7-dimethyl-2-ethyl-3H-imidazo[4,5-b]pyridine To a solution of the product of Step A (75 mg, 0.25 mmol) in 3 mL of DMF was added 11 mg (0.27 mmol, 1.1 eq) of 60% NaH, followed by 45 mg (0.30 mmol, 1.2 eq) of phthalic anhydride. This mixture was stirred for 16 hours and the DMF removed in vacuo. The resultant oil was flash column chromatographed with 15% of (10/1) mixture of methanol/NH$_4$OH in CHCl$_3$ to yield the titled compound (53 mg, 47%).

FAB-MS: m/e=453 (M+1).

$^1$H NMR (400 MHz, CD$_3$OD, ppm) d 8.13 (d, 1H); 7.66-7.71 (m, 3H); 7.51 (d, 1H); 7.28 (s, 2H); 7.14-7.16 (m, 2H); 7.03 (s, 1H); 6.49 (d, 1H); 5.64 (s, 2H); 2.86 (q, 2H); 2.62 (s, 3H); 2.60 (s, 3H); 1.24 (t, 3H).

EXAMPLE 3

3-[N-(2-carboxy-3-nitrobenzoyl)-5-indolyl]methyl-5,7-dimethyl-2-ethyl-3H-imidazo[4,5-b]pyridine Following the procedure of Example 2, Step B and replacing phthalic anhydride with 3-nitrophthalic anhydride the titled compound is prepared.

FAB-MS: m/e=498 (M+1).

$^1$H NMR (400 MHz, CD$_3$OD, ppm) d 8.46-8.51 (m, 3H); 7.89 (t, 3H); 7.31 (s, 1H); 7.24 (d, 1H); 7.06 (s, 1H); 6,.92 (d, 1H); 6.50 d, 1H); 5.68 (s, 2H); 2.91 (q, 2H); 2.63 (s, 3H); 2.62 (s, 3H); 1.29 (t, 3H).

EXAMPLE 4

3-[N-(2-carboxy-3,6-dichlorobenzoyl)-5-indolyl]methyl-5,7-dimethyl-2-ethyl-3H-imidazo[4,5-b]pyridine Following the procedure of Example 2, Step B and replacing phthalic anhydride with 3,6-dichlorophthalic anhydride the titled compound is prepared.

FAB-MS: m/e=521 (M+1).

$^1$H NMR (300 MHz, CD$_3$OD, ppm) d 8.40 (d, 1H); 7.55 (d, 1H); 7.43 (d, 1H); 7.28 (s, 1H); 7.18 (d, 1H); 7.02 (s, 1H); 6.97 (d, 1H); 6.52 (d, 1H); 5.64 (s, 2H); 2.85 (q, 2H); 2.62 (s, 3H); 2.60 (s, 3H); 1.25 (t, 3H).

EXAMPLE 5

3-[N-(2-carboxy-4,5-dichlorobenzoyl)-5-indolyl]methyl-5,7-dimethyl-2-ethyl-3H-imidazo[4,5-b]pyridine Following the procedure of Example 2, Step B and replacing phthalic anhydride with 4,5-dichlorophthalic anhydride the titled compound is prepared.

FAB-MS: m/e=521 (M+1).

$^1$H NMR (300 MHz, CD$_3$OD, ppm) d 8.25 (s, 1H); 7.65 (s, 1H); 7.18 (d, 1H); 7.02 (s, 1H); 6.91 (m, 1H); 6.53 (d, 1H); 5.64 (s, 2H); 2.86 (q, 2H); 2.65 (s, 3H); 2.62 (s, 3H); 1.27 (t, 3H).

EXAMPLE 6

3-[N-(2-carbamylbenzoyl)-5-indolyl]methyl-5,7-dimethyl-2-ethyl-3H-imidazo[4,5-b]pyridine To a solution of the product of Example 2, Step A (200 mg, 0.66 mmol) in 7 mL of DMF was added NaH (53 mg, 1.23 mmol) and the mixture stirred for a few minutes. Isatoic anhydride (160 mg, 0.99 mmol) was added to the reaction mixture and it was stirred for 16 hours. The solvent was removed in vacuo and the resultant residue was flash column chromatographed with 15% of (10/1) mixture of MeOH/NH$_4$OH in CHCl$_3$ to give titled compound (236 mg, 77%).

FAB-MS: m/e=468 (M+1).

$^1$H NMR (300 MHz, CD$_3$OD, ppm) d 8.47 (d, 1H); 8.31 (d, 1H); 8.10 (d, 1H); 7.86 (d, 1H); 7.42 (t, 1H); 7.29 (s, 1H); 7,13 (d, 1H); 7.08 (t, 1H); 7.03 (d, 1H); 6.62 (d, 1H); 5.63 (s, 2H); 2.86 (q, 2H); 2.61 (s, 3H); 2.57 (s, 3H); 1.24 (t, 3H).

EXAMPLE 7

3-[N-(2-methylcarbamoylbenzoyl)-5-indolyl]methyl-5,7-dimethyl-2-ethyl-3H-imidazo[4,5-b]pyridine To a solution of 12.1 mg of the product of Example 6 in CH$_2$Cl$_2$ at 0° C. was added 0.2 mL of 10% trimethylsilyl-diazomethane. After stirring for 10 minutes, 0.2 mL of acetic acid was added. The volatiles were removed in vacuo. The product was isolated using preparative TLC with 1:1 hexane/ethyl acetate.

FAB-MS: m/e=482 (M+1).

¹H NMR (300 MHz, CDCl₃, ppm) d 11.80 (s, 1H); 8.71 (d, 1H); 8.37 (d, 1H); 8.19 (d, 1H); 7.73 (d, 1H); 7.62 (t, 1H); 7.23 (d, 1H); 7.17 (t, 1H); 6.94 (s, 1H); 6.62 (d, 1H); 5.52 (s, 2H); 3.98 (s, 3H); 2.84 (q, 2H); 2.62 (s, 3H); 2.59 (s, 3H); 1.27 (t, 3H).

EXAMPLE 8

3-[N-(2-cyanobenzoyl)-5-indolyl]methyl-5,7-dimethyl-2-ethyl-3H-imidazo[4,5-b]pyridine Step A: Preparation of 2-Cyanobenzoyl Chloride A mixture of 2-cyanobenzoic acid (2 g, 13.6 mmol) and 15 ml of thionyl chloride was refluxed overnight. Excess thionyl chloride was removed in vacuo and the resultant 2-cyanobenzoyl chloride obtained as such as an off white solid was used in the above acylation.

Step B: Preparation of 3-[N-(2-cyanobenzoyl)-5-indolyl]methyl-5,7-dimethyl-2-ethyl-3H-imidazo[4,5-b]pyridine To a solution of the product of Example 2, Step A (250 mg, 0.82 mmol) in 3 mL of DMF was added 60% NaH (39 mg, 1 mmol, 1.2 eq). After stirring for 5 minutes, 2-cyanobenzoyl chloride (204 mg, 1.23 mmol, 1.5 eq) was added to the reaction mixture. The resultant solution was stirred for 16 hours and the DMF removed in vacuo. The resultant oil was flash chromatographed with 2:1 hexane/ethyl acetate to yield the titled compound (292 mg, 82%).

FAB-MS: m/e=434 (M+1).

¹H NMR (400 MHz, CDCl₃, ppm) d 8.30 (d, 1H); 7.84 (d, 1H); 7.64–7.73 (m, 3H); 7.23 (d, 2H); 6.99 (d, 1H); 6.89 (s, 1H); 6.52 (d, 1H); 5.56 (s, 2H); 2.78 (q, 2H); 2.63 (s, 3H); 2.58 (s, 3H); 1.29 (t, 3H).

EXAMPLE 9

3-[N-(2-tetrazol-5-yl-benzoyl)-5-indolyl]methyl-5,7-dimethyl-2-ethyl-3H-imidazo[4,5-b]pyridine To a solution of the product of Example 8, Step B (75 mg, 0.17 mmol) in 5 mL of toluene was added trimethyltin azide (43 mg, 0.21 mmol, 1.2 eq). The mixture was heated at reflux for 18 hours. Toluene was removed in vacuo and the resultant oil was dissolved in 5 mL of THF and treated with 0.5 mL of 2.5N HCl at 0° C. for 5 minutes. The volatiles were removed in vacuo and the resultant oil was flash chromatographed with 20% of 10/1 methanol/NH₄OH mixture in chloroform to yield the titled compound (48.2 mg, 60%).

FAB-MS: m/e=477 (M+1).

¹H NMR (300 MHz, CD₃OD, ppm) d 8.12 (br s, 1H); 7.96 (d, 1H); 7.55–7.70 (m, 3H); 7.20 (s, 1H); 7.08 (d, 1H); 6.98 (s, 1H); 6.87 (br s, 1H); 5.55 (s, 2H); 2.72 (q, 2H); 2.51 (s, 6H); 1.16 (t, 3H).

EXAMPLE 10

3-[N-(2-cyanobenzyl)-5-indolyl]methyl-5,7-dimethyl-2-ethyl-3H-imidazo[4,5-b]pyridine To a solution of the product of Example 2, Step A, (75 mg, 0.25 mmol) in 3 mL of DMF was added 11 mg (0.27 mmol, 1.1 eq) of 60% NaH followed by α-bromo-o-tolunitrile (58 mg, 0.30 mmol, 1.2 eq). The mixture was stirred for 16 hours and then concentrated in vacuo. The resultant oil was flash chromatographed with 1:1 hexane/ethyl acetate to yield the titled compound (98 mg, 95%).

FAB-MS: m/e=420 (M+1).

¹H NMR (300 MHz, CDCl₃, ppm) d 7.68 (d, 1H); 7.31–7.45 (m, 3H); 7.02 (d, 1H); 6.98 (s, 1H); 6.76 (d, 1H); 6.50 (d, 1H); 5.56 (s, 2H); 5.49 (s, 2H); 2.83 (q, 2H); 2.61 (s, 3H); 2.58 (s, 3H); 1.29 (t, 3H).

EXAMPLE 11

3-[N-(2-tetrazol-5-yl-benzyl)-5-indolyl]methyl-5,7-dimethyl-2-ethyl-3H-imidazo[4,5-b]pyridine Following the procedure of Example 9, but utilizing the product of Example 10, the titled compound was prepared.

FAB-MS: m/e=463 (M+1).

¹H NMR (400 MHz, CD₃OD, ppm) d 7.76 (s, 1H); 7.73 (d, 1H); 7.39 (t, 1H); 7.32 (d, 1H); 7.12 (d, 1H); 7.10 (d, 1H); 7.01 (s, 1H); 6.92 (dd, 1H); 6.73 (d, 1H); 6.41 (d, 1H); 5.69 (s, 2H); 5.60 (s, 2H); 2.87 (q, 2H); 2.62 (s, 3H); 2.61 (s, 3H); 1.22 (t, 3H).

EXAMPLE 12

3-[N-(2-cyano-6-chlorobenzyl)-5-indolyl]-dimethyl-2-ethyl-3H-imidazo[4,5-b]pyridine Step A: Preparation of 2-chloro-6-cyanobenzyl bromide To a refluxing solution of 3-chloro-2-methylbenzonitrile (2.0 g, 13.2 mmol) in 20 mL of CCl₄ was added 2.6 g (14.4 mmol, 1.1 eq) of N-bromosuccinimide and 0.2 g of AIBN. The solution was refluxed for 3 hours and then cooled, diluted with 500 mL of CH₂Cl₂ and washed with 200 mL of H₂O and 200 mL of brine. The organic phase was dried over MgSO₄, filtered and concentrated in vacuo. The resultant oil was flash chromatographed with 5:1 hexane/ethyl acetate to yield the titled compound (1.4 g, 46%) as a yellow oil.

FAB-MS: m/e=230 (M+1).

¹H NMR (400 MHz, CDCl₃, ppm) d 7.63 (dd, 1H); 7.58 (dd, 1H); 7.37 (t, 1H); 4.74 (s, 2H).

Step B: Preparation of 3-[N-(2-cyano-6-chlorobenzyl)-5-indolyl]methyl-5,7-dimethyl-2-ethyl-3H-imidazo[4,5-b]pyridine Following the procedure of Example 10 but replacing α-bromo-o-tolunitrile with the product of Step A the titled compound was prepared.

FAB-MS: m/e=454 (M+1).

¹H NMR (400 MHz, CDCl₃, ppm) d 7.63 (d, 2H); 7.40 (t, 1H); 7.34 (d, 1H); 7.31 (s, 1H); 7.01 (m, 2H); 6.87 (s, 1H); 6.40 (d, 1H); 5.52 (s, 2H); 2.78 (q, 2H); 2.61 (s, 3H); 2.58 (s, 3H); 1.26 (t, 3H).

EXAMPLE 13

3-[N-(2-tetrazol-5-yl-6-Chlorobenzyl)-5-indolyl]methyl-5,7-dimethyl-2-ethyl-3H-imidazo[4,5-b]pyridine Following the procedure of Example 9 but utilizing the product of Example 12 the titled compound was prepared.

¹H NMR (400 MHz, CD₃OD, ppm) d 7.61 (d, 1H); 7.57 (d, 1H); 7.46 (t, 1H); 7.21 (s, 1H); 7.12 (d, 1H); 7.06 (s, 1H); 6.89 (dd, 1H); 6.72 (d, 1H); 6.18 (d, 1H); 5.69 (s, 2H); 5.58 (s, 2H); 2.87 (q, 2H); 2.61 (s, 3H); 2.59 (s, 3H); 1.19 (s, 3H).

EXAMPLE 14

3-[N-(2-carbomethoxybenzyl)-5-indolyl]methyl-5,7-dimethyl-2-ethyl-3H-imidazo[4,5-b]pyridine Step A: Preparation of Methyl-2-bromomethylbenzoate To a solution of 2.3 g (15.3 mmol) of methyl o-methylbenzoate (methyl o-toluate) in 20 mL of refluxing CCl₄ was added 3 g of N-bromosuccinimide and 0.10 g AIBN. After 2.5 hours the mixture was cooled, diluted with 500 mL of CH₂Cl₂ and washed with 200 mL of H₂O and 200 mL of brine. The organic phase was dried over MgSO₄, filtered and concentrated in vacuo. The resultant oil was flash chromatographed with 5:1 hexane/ethyl acetate to yield the titled compound (2.56 g, 73%).

FAB-MS: m/e=230 (M+1).

$^1$H NMR (300 MHz, CDCl$_3$, ppm) d 7.97 (d, 1H); 7.51 (d, 1H); 7.48 (d, 1H); 7.39 (dd, 1H); 4.96 (s, 2H); 3.93 (s, 3H).

Step B: Preparation of 3-[N-(2-carbomethoxybenzyl)-5-indolyl]methyl-5,7-dimethyl-2-ethyl-3H-imidazo[4,5-b]pyridine Following the procedure of Example 10 but replacing α-bromo-o-tolunitrile with the product of Step A the titled compound was prepared.

FAB-MS: m/e=453 (M+1).

$^1$H NMR (300 MHz, CDCl$_3$, ppm) d 8.02 (m, 1H); 7.39 (s, 1H); 7.24–7.33 (m, 2H); 7.10 (d, 1H); 7.08 (s, 1H); 6.99 (d, 1H); 6.89 (s, 1H); 6.50 (d, 2H); 6.42 (t, 1H); 5.74 (s, 2H); 5.57 (s, 2H); 3.92 (s, 3H); 2.82 (q, 2H); 2.63 (s, 3H); 2.59 (s, 3H); 1.32 (t, 3H).

EXAMPLE 15

3-[N-(2-carboxybenzyl)-5-indolyl]methyl-5,7-dimethyl-2-ethyl-3H-imidazo[4,5-b]pyridine To a solution of 75 mg (0.17 mmol) of the product of Example 14, Step B in 3 mL of methanol was added 2.0 mL of 1N NaOH. The mixture was stirred for 16 hours. The volatiles were removed in vacuo and the water removed azeotropically with toluene. The clear oil was flash chromatographed with 80:20:2 CHCl$_3$/methanol/NH$_4$OH to yield the titled compound (58 mg, 80%).

FAB-MS: m/e=439 (M+1).

$^1$H NMR (400 MHz, CD$_3$OD, ppm) d 7.89 (d, 1H); 7.31 (s, 1H); 7.17–7.25 (m, 4H); 7.00 (s, 1H); 6.93 (d, 1H); 6.44 (s, 1H); 6.43 (d, 1H); 5.74 (s, 2H); 5.60 (s, 2H); 2.86 (q, 2H); 2.61 (s, 3H); 2.60 (s, 3H); 1.21 (t, 3H).

EXAMPLE 16

3-[N-(2-carbomethoxy-4,5-dichlorobenzyl)-5-indolyl]-methyl-5,7-dimethyl-2-ethyl-3H-imidazo[4,5-b]pyridine Step A: Preparation of 2-carbomethoxy-4,5-dichlorobenzoic acid To a solution of 4,5-dichlorophthalic anhydride (1.0 g, 4.61 mmol) in 15 mL of methanol was added 0.25 g (9.22 mmol, 2.0 eq) of sodium methoxide. The suspension was stirred for 3 days and the methanol was removed in vacuo. The resultant white solid was suspended in 500 mL of CH₂Cl₂ and washed with 1N HCl. The organic phase was dried over anhydrous Na₂SO₄, filtered and the volatiles removed in vacuo to yield 1.06 g (92.5%) of the titled compound as a white powder.

FAB-MS: m/e=249 (M+1).

$^1$H NMR (300 MHz, CD$_3$OD, ppm) d 8.26 (s, 1H); 8.11 (s, 1H); 4.10 (s, 3H).

Step B: Preparation of Methyl 4,5-dichloro-2-(hydroxy-methyl)benzoate

To a solution of the product of Step A (1.06 g, 4.28 mmol) in 5 mL of THF at 0° C. was added borane-methyl sulfide (6.42 mL of 2M solution in THF, 12.84 mmol, 3.0 eq). The reaction was allowed to warm to room temperature. After 16 hours the reaction was cooled to 0° C. and quenched with methanol. The volatiles were removed in vacuo and the oil flash chromatographed with 2:1 hexane/ethyl acetate to yield the titled compound (169 mg, 17%). Approximately 80% of the starting material was also recovered.

FAB-MS: m/e=235 (M+1).

$^1$H NMR (300 MHz, CDCl$_3$, ppm) d 8.08 (s, 1H); 7.62 (s, 1H); 4.79 (d, 2H); 3.94 (s, 3H); 3.54 (t, 1H).

Step C: Preparation of Methyl 2-(bromoethyl)-4,5-dichlorobenzoate

To a solution of 169 mg (0.72 mmol) of the product of Step B in 3 mL of CH₂Cl₂ at 0° C. was added 283 mg (1.08 mmol, 1.5 eq) of triphenylphosphine and 360 mg (1.08 mmol, 1.5 eq) of carbon tetrabromide. The mixture was stirred for 16 hours and quenched with methanol. The reaction was concentrated in vacuo and the resultant oil was flash chromatographed with 2:1 hexane/ethyl acetate to afford the titled compound (107 mg, 50%) as a brownish orange oil.

FAB-MS: m/e=297 (M+1).

$^1$H NMR (300 MHz, CDCl$_3$, ppm) d 8.06 (s, 1H); 7.58 (s, 1H); 4.86 (s, 2H); 3.94 (s, 3H).

Step D: Preparation of 3-[N-(2-carbomethoxy-4,5-dichlorobenzyl)-5-indolyl]methyl-5,7-dimethyl-2-ethyl-3H-imidazo[4,5-b]pyridine Following the procedure of Example 10 but replacing α-bromo-o-tolunitrile with the product of Step C the titled compound was prepared.

FAB-MS: m/e=521 (M+1).

$^1$H NMR (300 MHz, CDCl$_3$, ppm) d 8.12 (s, 1H); 7.41 (s, 1H); 7.11 (d, 1H); 6.98–7.08 (m, 2H); 6.89 (s, 1H); 6.52 (d, 1H); 6.47 (s, 1H); 5.68 (s, 2H); 5.55 (s, 2H); 3.93 (s, 3H); 2.89 (q, 2H); 2.62 (s, 3H); 2.59 (s, 3H); 1.25 (t, 3H).

EXAMPLE 17

3-[N-(2-cyanobenzoyl)-5-dihydroindolyl]methyl-5,7-dimethyl-2-ethyl-3H-imidazo[4,5-b]pyridine Step A: Preparation of 3-(5-dihydroindolyl)methyl-5-7-dimethyl-2-ethyl-3H-imidazo[4,5-b]pyridine To a solution of 5 (500 mg, 1.64 mmol) in 4 mL of acetic acid was slowly added NaCNBH₃ (114 mg, 1.81 mmol, 1.1 eq). After 45 minutes the reaction was diluted with 150 mL of H₂O and neutralized carefully with aqueous solution of saturated NaHCO₃. The pH was adjusted to 9 with the addition of solid NaOH and then extracted with 3×200 mL of CH₂Cl₂. The combined extracts were dried over Na₂SO₄, filtered and concentrated in vacuo. Flash column chromatography of crude material eluted with 100% ethyl acetate provided 9 (377 mg, 75%) and the titled compound (115 mg, 23%).

FAB-MS: m/e=307 (M+1).

$^1$H NMR (300 MHz, CDCl$_3$, ppm) d 6.88 (s, 2H); 6.83 (d, 1H); 6.52 (d, 1H); 5.34 (s, 2H); 3.75 (brs, 1H); 3.51 (t, 2H); 2.92 (t, 2H); 2.80 (q, 2H); 2.62 (s, 3H); 2.60 (s, 3H); 1.30 (t, 3H).

Step B: Preparation of 3-[N-(2-cyanobenzoyl)-5-dihydroindolyl]methyl-5,7-dimethyl-2-ethyl-3H-imidazo[4,5-b]pyridine To a solution of the product of Step A (25 mg, 0.08 mmol) in 1.5 mL of CH₂Cl₂ was added 5.0 mg (0.04 mmol, 0.05 eq) of 4-dimethylaminopyridine and 15.0 mg (0.09 mmol, 1.1 eq) of 2-cyanobenzoyl chloride. The reaction was stirred for 1 hour and then diluted with 200 mL of CH₂Cl₂ and washed with 100 mL of aqueous saturated NaHCO₃ solution and 100 mL of brine. The organic phase was dried over MgSO₄, filtered and concentrated in vacuo. The resultant oil was flash chromatographed with ethyl acetate to yield the titled compound 19.9 mg (56%).

FAB-MS: m/e=436 (M+1).

$^1$H NMR (300 MHz, CDCl$_3$, ppm) d 8.20 (d, 1H); 7.65-7.80 (m, 2H); 7.64 (d, 2H); 7.13 (d, 1H); 6.88 (s, 2H); 5.46 (s, 2H); 3.87 (t, 2H); 3.17 (t, 2H); 2.79 (q, 2H); 2.63 (s, 3H); 2.58 (s, 3H); 1.28 (t, 3H).

EXAMPLE 18

3-[N-(2-tetrazol-5-yl-benzoyl)-5-dihydroindolyl]methyl-5,7-dimethyl-2-ethyl-3H-imidazo[4,5-b]pyridine Following the procedure of Example 9 but utilizing the product of Example 17 the titled compound was prepared.

FAB-MS: m/e=479 (M+1).

$^1$H NMR (400 MHz, CD$_3$OD, ppm) d 8.10 (d, 1H); 7.91-7.99 (m, 2H); 7.60-7.72 (m, 2H); 7.57 (d, 1H); 7.04 (s, 1H); 7.00 (s, 1H); 5.53 (s, 2H); 3.76 (t, 2H); 2.99 (t, 2H); 2.90 (q, 2H); 2.61 (s, 3H); 2.59 (s, 3H), 1.29 (t, 3H).

EXAMPLE 19

3-[N-(2-acetoxybenzoyl)-5-dihydroindolyl]methyl-5,7-dimethyl-2-ethyl-3H-imidazo[4,5-b]pyridine To a solution of 50 mg (0.16 mmol) of the product of Example 17, Step A and 36 mg (0.18 mmol, 1.1 eq) of o-salicyloyl chloride in 2 mL of CH$_2$Cl$_2$ was added 2 mL of aqueous solution of saturated NaHCO$_3$. The biphasic mixture was stirred for 16 hours and then diluted with 100 mL of CH$_2$Cl$_2$, washed with 50 mL of aqueous solution of saturated NaHCO$_3$ and 50 mL of brine. The organic phase was dried over MgSO$_4$, filtered and concentrated in vacuo. The resultant oil was flash chromatographed with ethyl acetate to yield 55 mg (72%) of the titled compound.

FAB-MS m/e=469 (M+1).

$^1$H NMR (300 MHz, CDCl$_3$, ppm) d 8.17 (d, 1H); 7.34-7.50 (m, 2H); 7.28 (t, 2H); 7.20 (d, 1H); 7.11 (d, 1H); 6.89 (s, 2H); 5.43 (d, 2H); 3.89 (t, 2H); 3.02 (t, 2H); 2.79 (q, 2H); 2.63 (s, 3H); 2.59 (s, 3H); 2.18 (s, 3H); 1.32 (t, 3H).

EXAMPLE 20

3-[N-(2-acetoxybenzoyl)-5-indolyl]methyl-5,7-dimethyl-2-ethyl-3H-imidazo[4,5-b]pyridine To a refluxing solution of 220 mg (0.47 mmol) of the product of Example 19 in 5 mL of 1,4-dioxane was added 320 mg (1.41 mmol, 3.0 eq) of 2,3-dichloro-5,6-dicyano-1,4-quinone. The mixture was refluxed for 6 hours then cooled and concentrated in vacuo. The resultant oil was flash chromatographed with ethyl acetate to yield 50 mg (23%) of the titled compound as a white solid.

FAB-MS: m/e=467 (M+1).

$^1$H NMR (300 MHz, CDCl$_3$, ppm) d 8.31 (d, 1H); 7.60 (t, 1H); 7.55 (d, 1H); 7.37 (t, 1H); 7.28 (m, 3H); 7.11 (d, 1H); 6.92 (s, 1H); 6.48 (d, 1H); 5.57 (s, 2H); 2.83 (q, 2H); 2.64 (s, 3H); 2.58 (s, 3H); 2.07 (s, 3H); 1.30 (t, 3H).

EXAMPLE 21

3-[N-(2-carboxybenzoyl)-5-dihydroindolyl]methyl-5,7-dimethyl-2-ethyl-3H-imidazo[4,5-b]pyridine To a solution of the product of Example 17, Step A (25 mg, 0.08 mmol) in 1.5 mL of CH$_2$Cl$_2$ was added 5.0 mg (0.04 mmol, 0.05 eq) of 4-dimethylaminopyridine and 13.3 mg (0.09 mmol, 1.1 eq) of phthalic anhydride. The reaction was stirred for 2 hours and then concentrated in vacuo. The resultant oil was flash chromatographed with 80:20:2 CHCl$_3$/methanol/NH$_4$OH to yield 31.4 mg (84%) of the titled compound.

FAB-MS: m/e=455 (M+1)

$^1$H NMR (300 MHz, CD$_3$OD, ppm) d 8.10 (d, 1H); 7.62 (t, 2H); 7.46 (m, 2H); 7.31 (s, 1H); 6.89 (m, 2H); 5.42 (s, 2H); 3.57 (t, 2H); 2.88 (t, 2H); 2.77 (q, 2H); 2.56 (s, 3H); 2.51 (s, 3H); 1.27 (t, 3H).

EXAMPLE 22

3-[N-(2-carboxy-3,6-dichlorobenzoyl)-5-dihydroindolyl]methyl-5,7-dimethyl-2-ethyl-3H-imidazo[4,5-b]pyridine Following the procedure of Example 21, but replacing phthalic anhydride with 3,6-dichlorophthalic anhydride the titled compound was prepared.

FAB-MS: m/e=522 (M+1)

$^1$H NMR (300 MHz, CD$_3$OD, ppm) d 8.12 (d, 1H); 7.70 (s, 1H); 7.55-7.37 (m, 2H); 7.05 (two overlapping s, 2H); 5.50 (s, 2H); 4.05 (m,1H), 3.82 (m, 1H); 3.10 (m, 2H); 2.875 (q, 2H); 2.64 (s, 3H); 2.605 (s, 3H); 1.30 (t, 3H).

EXAMPLE 23

3-[N-(2-carboxy-4,5-dichlorobenzoyl)-5-dihydroindolyl]methyl-5,7-dimethyl-2-ethyl-3H-imidazo[4,5-b]pyridine Following the procedure of Example 21, but replacing phthalic anhydride with 4,5- dichlorophthalic anhydride the titled compound was prepared.

FAB-MS: m/e=522 (M+1)

$^1$H NMR (300 MHz, CD$_3$OD, ppm) δ8.11 (m, 2H); 7.45 (s, 1H); 6.98 (d, 1H); 6.95 (s, 1H); 6.94 (d, 1H); 5.48 (s, 2H); 3.705 (t, 2H); 2.98 (t, 2H); 2.84 (q, 2H); 2.62 (s, 3H); 2.585 (s, 3H); 1.294 (t, 3H).

EXAMPLE 24

3-[N-(1-carbomethoxy-1-phenyl)methyl-5-dihydroindolyl]methyl-5,7-dimethyl-2-ethyl-3H-imidazo[4,5-b]pyridine To a solution of the product of Example 17, Step A (64.5 mg, 0.198 mmol) in DMF was added NaH (16 mg, 2 equiv) and the mixture stirred for 15 min. Methyl α-bromophenylacetate (97 mg, 2.2 equiv) was added to the reaction mixture and stirred for 24 h. The DMF was removed in vacuo and residue was flash chromatographed using 60% ethyl acetate in hexane as eluent to afford the titled compound (88 mg, 98%).

FAB-MS: m/e=455 (M+1)

$^1$H NMR (300 MHz, CD$_3$Cl$_3$, ppm) δ7.35 (s, 5H); 6.86 (d, 1H); 6.34 (two overlapping s, 2H); 6.31 (d, 1H); 5.33 (s, 2H); 5.22 (s, 1H); 3.73 (s, 3H); 3.13-3.04 (m, 1H); 2.88-2.75 (m, 1H); 2.8 (q, 2H), 2.73 (m, 2H); 2.63 (s, 3H), 2.6 (s, 3H), 1.3 (t, 3H).

EXAMPLE 25

3-[N-(1-carboxy-1-phenyl)methyl-5-dihydroindolyl]methyl-5,7-dimethyl-2-ethyl-3H-imidazo[4,5-b]pyridine Methyl ester, the product of Example 24, (60 mg, 0.132 mmol) was treated with 1N NaOH in methanol for 24 h. The volatiles were removed in vacuo and the residue was flash chromatographed with 15% of 9/1 methanol/NH$_4$OH mixture in chloroform as eluent to give the titled acid (46.5 mg, 80%).

FAB-MS: m/e=441 (M+1)

¹H NMR (300 MHz, CD₃OD, ppm) δ7.73 (m), 7.63 (m), 7.5-7.27 (m), 7.2-6.96 (m), 6.35 (d), 6.2 (d), 5.65 (d), 6.39 (m, 2H), 3.58 (m, 2H), 2.89 (q, 2H), 2.66 (s, 3H), 2.65 (s, 3H), 1.32 (t, 3H).

EXAMPLE 26

3-[N-(1-cyano-1-phenyl)methyl-5-dihydroindolyl]methyl-5,7-dimethyl-2-ethyl-3H-imidazo[4,5-b]pyridine A mixture of the product of Example 17, Step A (50 mg, 0.153 mmol), benzaldehyde (0.1 mL, 7.4 equiv), and KCN (74 mg, 7.4 equiv) in AcOH and methanol was stirred for five days. The volatiles were removed in vacuo and the resultant solid was flash chromatographed with 50% ethyl acetate in hexane to afford the titled compound (60 mg, 92%).

FAB-MS: m/e=422 (M+1)

¹H NMR (300 MHz, CDCl₃, ppm) δ7.58 (d, 2H), 7.427 (m, 3H), 6.94 (d, 1H), 6.902 (two overlapping s, 2H), 6.533 (d, 1H), 5.697 (s, 1H), 5.381 (s, 2H), 3.33-3.14 (m, 2H), 2.98-2.3 (m, 2H), 2.85 (q, 2H), 2.62 (s, 3H), 2.602 (s, 3H), 1.307 (t, 3H).

EXAMPLE 27

3-[N-(1-cyano-1-o-tolyl)methyl-5-dihydroindolyl]-methyl-5,7-dimethyl-2-ethyl-3H-imidazo[4,5-b]pyridine The titled compound was prepared from the product of Example 17, Step A, (120 mg, 0.368 mmol), o-tolualdehyde, KCN and AcOH according to the procedure of Example 26 in 41% yield (65 mg).

FAB-MS: m/e=436 (M+1)

¹H NMR (300 MHz, CDCl₃, ppm) δ7.653 (d, 1H), 7.4-7.15 (m, 3H), 6.985 (d, 1H), 6.897 (two overlapping s, 2H), 6.633 (d, 1H), 5.731 (s, 1H), 5.382 (s, 2H), 3.28-3.16 (m, 1H), 3.0 (dt, 1H), 2.95-2.7 (m, 2H), 2.8545 (q, 2H), 2.62 (s, 3H), 2.602 (s, 3H), 2.343 (s, 3H), 1.327 (t, 3H).

EXAMPLE 28

3-[N-(1-cyano-1-m-tolyl)methyl-5-dihydroindolyl]-methyl-5,7-dimethyl-2-ethyl-3H-imidazo[4,5-b]pyridine The titled compound was prepared from the product of Example 17, Step A (106 mg, 0.325 mmol), m-tolualdehyde, KCN and AcOH according to the procedure of Example 26 in 84% yield (118.3 mg).

FAB-MS: m/e=436 (M+1)

¹H NMR (400 MHz, CDCl₃, ppm) d 7.35 (d, 1H), 7.285 (t, 1H), 7.18 (d, 1H), 6.92 (d, 1H), 6.87 (two overlapping s, 2H), 6.5 (d, 1H), 5.63 (s, 1H), 5.36 (s, 2H), 3.26-3.13 (m, 2H), 2.92-2.85 (m, 2H), 2.825 (q, 2H), 2.62 (s, 3H), 2.585 (s, 3H), 2.37 (s, 3H), 1.3 (t, 3H).

EXAMPLE 29

3-[N-(1-cyano-1-p-tolyl)methyl-5-dihydroindolyl]methyl-5,7-dimethyl-2-ethyl-3H-imidazo[4,5-b]pyridine The titled compound was prepared from the product of Example 17, Step A (96 mg, 0.2944 mmol), p-tolualdehyde, KCN, and AcOH in methanol according to the procedure of Example 26 in 75% yield (96 mg).

FAB-MS: m/e=436 (M+1)

¹H NMR (400 MHz, CDCl₃, ppm) δ7.425 (d, 2H), 7.21 (d, 2H), 6.915 (d, 1H), 6.86 (s, 2H), 6.52 (d, 1H), 5.63 (s, 1H), 5.36 (s, 2H), 3.26-3.1 (m, 2H), 2.93-2.83 (m, 2H), 2.78 (q, 2H), 2.61 (s, 3H), 2.57 (s, 3H), 2.35 (s, 3H), 1.3 (t, 3H).

EXAMPLE 30

3-[N-(1-tetrazol-5-yl-1-phenyl)methyl-5-dihydroindolyl]methyl-5,7-dimethyl-2-ethyl-3H-imidazo[4,5-b]pyridine Following the procedure of Example 9, but utilizing the product of Example 26, the titled compound was prepared.

FAB-MS: m/e=465 (M+1)

¹H NMR (300 MHz, CDCl₃, ppm) δ7.43-7.27 (m, 5H), 7.05 (s, 1H), 6.9 (s, 1H), 6.83 (d, 1H), 6.32 (d, 1H), 6.18 (s, 1H), 5.65 (s), 5.43 (s, 2H), 3.73-3.58 (m), 3.55-3.3 (m), 3.3-3.15 (m), 2.88 (q, 2H), 2.65 (s, 6H), 1.3 (t, 3H).

EXAMPLE 31

3-(5-indolyl)methyl-7-methyl-2-propyl-3H-imidazo[4,5-b]pyridine

Step A: Preparation of 2,3-diamino-4-picoline (cf. Lappin, G. R.; Slezak, F. B. J. Am. Chem. Soc., 1950, 72, 2806-7)

To a slurry of 2-amino-4-methyl-3-nitropyridine (10.0 g, 65.3 mmol) in 350 mL of 95% EtOH was added 500 mg of a 10% Pd/C catalyst. The mixture was stirred under a H₂ atmosphere (1 atm) for 36 hours. Filtration and evaporation gave 8.05 g of a black solid which was used directly in the next step.

Step B: Preparation of 7-methyl-2-propylimidazo [4,5-b]pyridine (cf. Lappin, G. R.; Slezak, F. B. J. Am. Chem. Soc., 1950, 72, 2806-7)

A mixture of butyric acid (6.57 mL, 71.9 mmol), 2,3-diamino-4-picoline (8.05 g, 65.4 mmol), and polyphosphoric acid (50 g) was heated to 100° C. with stirring for 3 hours, and monitored by tlc of NH₄OH neutralized aliquots. Basification (NH₄OH), extraction (CH₂Cl₂, 4×50 mL), drying (K₂CO₃), purification (by filtering through 100 g silica gel, EtOAc elution), and concentration gave 10.0 g (87%) of the title compound as an amorphous tan solid which was judged pure by ¹H NMR and tlc: mp 110°-112° C. (without recrystallization).

¹H NMR (300 MHz, CDCl₃, ppm): δ8.13 (d, 1H, J=5 Hz), 7.01 (d, 1H, J=5 Hz), 3.01 (t, 2H, J=7.8 Hz), 2.67 (s, 3H), 2.07-1.93 (m, 2H), 1.06 (t, 3H, J=7.5 Hz).

Step C: Preparation of 3-(5-indolyl)methyl-7-methyl-2-propyl-3H-imidazo[4,5-b]pyridine Following the procedures of Example 1, Steps D through F, followed by the procedure of Example 2, Step A the title compound can be prepared.

Examples 32 through 64 can be prepared as indicated in the Table below.

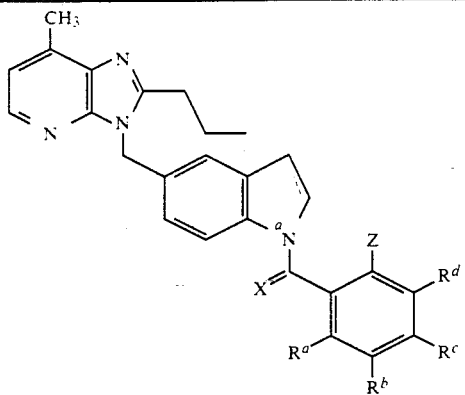

| # | a | X | $R^a$ | $R^b$ | $R^c$ | $R^d$ | Z | Utilizing the product of Example # and the procedure(s) of Example # |
|---|---|---|---|---|---|---|---|---|
| 32 | single bond | O | H | H | H | H | CO₂H | 31/2, Step B |
| 33 | single bond | O | H | H | H | NO₂ | CO₂H | 31/3 |
| 34 | single bond | O | Cl | H | H | Cl | CO₂H | 31/4 |
| 35 | single bond | O | H | Cl | Cl | H | CO₂H | 31/5 |
| 36 | single bond | O | H | H | H | H | NHCO₂H | 31/6 |
| 37 | single bond | O | H | H | H | H | NHCO₂CH₃ | 36/7 |
| 38 | single bond | O | H | H | H | H | CN | 31/8 |
| 39 | single bond | O | H | H | H | H | 1H-tetrazol-5-yl | 38/9 |
| 40 | single bond | H, H | H | H | H | H | CN | 31/10 |
| 41 | single bond | H, H | H | H | H | H | 1H-tetrazol-5-yl | 40/11 |
| 42 | single bond | H, H | Cl | H | H | H | CN | 31/12 |
| 43 | single bond | H, H | Cl | H | H | H | 1H-tetrazol-5-yl | 42/13 |
| 44 | single bond | H, H | H | H | H | H | CO₂CH₃ | 31/14 |
| 45 | single bond | H, H | H | H | H | H | CO₂H | 44/15 |
| 46 | single bond | H, H | H | Cl | Cl | H | CO₂CH₃ | 31/16 |
| 47 | single bond | H, H | H | Cl | Cl | H | CO₂H | 46/15 |
| 48 | absent | O | H | H | H | H | CN | 31/17 |
| 49 | absent | O | H | H | H | H | 1H-tetrazol-5-yl | 48/18 |
| 50 | absent | O | H | H | H | H | OC(=O)CH₃ | 48, Step A/19 |
| 51 | single bond | O | H | H | H | H | OC(=O)CH₃ | 50/20 |
| 52 | absent | O | H | H | H | H | CO₂H | 48, Step A/21 |
| 53 | absent | O | Cl | H | H | Cl | CO₂H | 48, Step A/22 |
| 54 | absent | O | H | Cl | Cl | H | CO₂H | 48, Step A/23 |
| 55 | absent | H, CO₂CH₃ | H | H | H | H | H | 48, Step A/24 |
| 56 | absent | H, CO₂H | H | H | H | H | H | 55/25 |
| 57 | absent | H, CN | H | H | H | H | H | 48, Step A/26 |
| 58 | absent | H, CN | H | H | H | H | CH₃ | 48, Step A/27 |
| 59 | absent | H, CN | H | H | H | CH₃ | H | 48, Step A/28 |
| 60 | absent | H, CN | H | H | CH₃ | H | H | 48, Step A/29 |
| 61 | absent | H, 1H-tetrazol-5-yl | H | H | H | H | H | 57/30 |
| 62 | absent | H, 1H-tetrazol-5-yl | H | H | H | H | CH₃ | 58/30 |
| 63 | absent | H, 1H-tetrazol-5-yl | H | H | H | CH₃ | H | 59/30 |
| 64 | absent | H, 1H-tetrazol-5-yl | H | H | CH₃ | H | H | 60/30 |

EXAMPLE 65

5-Carbomethoxy-2-ethyl-3-[(5-indolyl)methyl-7-methyl-3H-imidazo[4,5-b]pyridine

Step A: Preparation of 2-ethyl-7-methylimidazo[4,5-b]pyridine-4-oxide

A solution of 28 g (174 mmol) of 2-ethyl-7-methylimidazo[4,5-b]pyridine prepared according to Example 1, Steps A and B, but substituting propionic acid in place of butyric acid in Step B (described in European Patent Application No. 400,974, May 12, 1990) and m-chloroperbenzoic acid (80–90%, 44.6 g) in CHCl₃ (300 mL) was heated at reflux for 0.5 hours. The mixture was concentrated and purified (SiO₂, 100% CH₂Cl₂ gradient to 30% CH₂Cl₂/MeOH) to give 29.8 g of the title compound as a solid.

¹H NMR (300 MHz, CD₃OD, ppm): δ8.13 (d, 1H, J=6 Hz), 7.13 (d, 1H, J=6 Hz), 3.01 (q, 2H, J=7.5 Hz), 2.60 (s, 3H), 1.46 (t, 3H, J=7.5 Hz).

Step B: Preparation of 5-chloro-2-ethyl-7-methylimidazo[4,5-b]pyridine

A mixture of 29.75 g (0.168 mol) of the product of Step A, CHCl₃ (25 mL) and POCl₃ (160 mL) was heated to 80° C. for 1 hour. After pouring over ice, the mixture was neutralized by careful addition of NH₄OH and extracted with EtOAc. Concentration gave 23.8 g of the title compound as a solid.

¹H NMR (250 MHz, CDCl₃, ppm): δ7.07 (s, 1H) 3.10 (q, 2H, J=7.5 Hz), 2.67 (s, 3H), 1.48 (t, 3H, J=7.5 Hz).

Step C: Preparation of 5-bromo-2-ethyl-7-methylimidazo[4,5-b]pyridine

A mixture of 22.2 g (0.113 mol) of the product of Step B in 30% HBr-HOAc was heated to 100° C. for 19 hours. The mixture was poured onto ice, neutralized with NH₄OH, extracted (5×EtOAc), and the organic layers were concentrated to give 15 g (1ˢᵗ crop) of the title compound as a solid after crystallization from EtOAc.

$^1$H NMR (300 MHz, CDCl$_3$, ppm): δ7.22 (s, 1H) 3.13 (q, 2H, J=7.5 Hz), 2.66 (s, 3H), 1.47 (t, 3H, J=7.5 Hz).

Step D: Preparation of 3-benzyl-5-bromo-2-ethyl-7-methylimidazo[4,5-b]pyridine

To a solution of 10 g (39 mmol) of the product of Step C in DMF (70 mL) at rt was added NaH (1.3 g of an 80% oil dispersion, 43 mmol). After 20 minutes benzyl bromide (5.15 mL, 43 mmol) was added and the reaction was stirred for 16 hours. The mixture was poured onto 500 g of ice and the solid residue was filtered, washed with water and air dried to give 13 g of the title compound.

$^1$H NMR (300 MHz, CDCl$_3$, ppm): δ7.33-7.22 (m, 3H), 7.19 (s, 1H), 7.11-7.07 (m, 2H), 5.42 (s, 2H), 2.76 (q, 2H, J=7.5 Hz), 2.63 (s, 3H), 1.29 (t, 3H, J=7.5 Hz).

Step E: Preparation of 3-benzyl-5-cyano-2-ethyl-7-methylimidazo[4,5-b]pyridine

A mixture of 620 mg (1.8 mmol) of the product of Step D and CuCN (806 mg, 9.0 mmol) was heated in pyridine (4 mL) at reflux for 10 hours under nitrogen. The reaction was cooled, then water (50 mL), KCN (1.17 g), and EtOAc (20 mL) were added and the mixture was heated to 50° C. for 5 min. Cooling and extraction with EtOAc (2×50 mL) gave 467 mg of the title compound as a tan solid.

$^1$H NMR (400 MHz, CDCl$_3$, ppm): δ7.40 (s, 1H), 7.35-7.20 (m, 3H), 7.18-7.07 (m, 2H), 5.44 (s, 2H), 2.83 (q, 2H, J=7.5 Hz), 2.67 (s, 3H), 1.32 (t, 3H, J=7.5 Hz).

Step F: Preparation of methyl 3-benzyl-2-ethyl-7-methylimidazo[4,5-b]pyridine-5-carboxylate A solution of 440 mg (1.59 mmol) of the product of Step E in H$_2$SO$_4$ (4 mL) and H$_2$O (4 mL) was heated to 80° C. for 8 hours. The reaction was cooled, MeOH (150 mL) was added, then conc NH$_4$OH was added until the mixture turned basic. The white solid (NH$_4$)$_2$SO$_4$ was filtered and washed with MeOH. The water and MeOH were removed in vacuo and and the residue was taken up in MeOH and then filtered to remove any remaining (NH$_4$)$_2$SO$_4$. After concentrating, and removal of water from the residue by evaporation from toluene, anhydrous 3% HCl-MeOH (50 mL) was added and the mixture was stirred overnight at rt. Filtration, concentration, and extraction from 5% aqueous Na$_2$CO$_3$ with CH$_2$Cl$_2$ gave 750 mg of the crude title compound as a solid. $^1$H NMR (300 MHz, CDCl$_3$, ppm): δ7.93 (s, 1H) 7.38-7.29 (m, 3H), 7.12-7.03 (m, 2H), 5.53 (s, 2H), 3.96 (s, 3H), 2.78 (q, 2H, J=7.5 Hz), 2.70 (s, 3H), 1.29 (t, 3H, J=7.5 Hz).

Step G: Preparation of methyl 2-ethyl-7-methylimidazo[4,5-b]pyridine-5-carboxylate A mixture of 750 mg of the crude product of Step F in MeOH (30 mL), concentrated aqueous HCl (1 mL), and 100 mg of moist Pearlman's catalyst were shaken under 1 atm. H$_2$ for 24 hours. The reaction was incomplete so 100 mg more of the catalyst was added and the reaction was shaken as described above for an additional 24 hours. Filtration, concentration, and extraction from dilute NH$_4$OH with EtOAc followed by drying (Na$_2$SO$_4$), concentration, and purification (SiO$_2$, 5% MeOH/EtOAc) gave 250 mg of the title compound as a solid.

$^1$H NMR (400 MHz, CDCl$_3$, ppm): δ7.90 (s, 1H), 4.00 (s, 3H), 3.10 (q, 2H, J=7.5 Hz), 2.71 (s, 3H), 1.38 (t, 3H, J=7.5 Hz).

Step H: Preparation of 5-Carbomethoxy-2-ethyl-3-[(5-indolyl)methyl]-7-methyl-3H-imidazo[4,5-b]pyridine Following the procedures of Example 1, Steps D through F, followed by the procedure of Example 2, Step A the titled compound can be prepared.

Examples 66 through 98 can be prepared as indicated in the Table below.

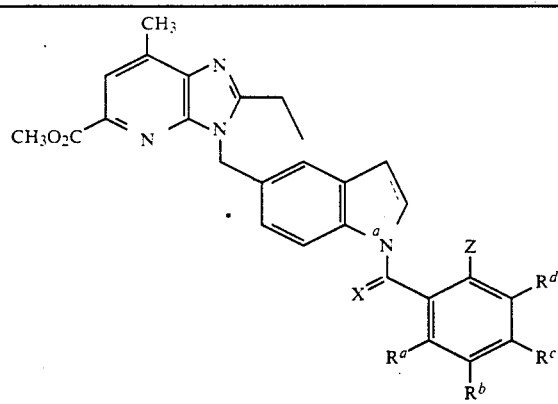

| # | a | X | R$^a$ | R$^b$ | R$^c$ | R$^d$ | Z | Utilizing the product of Example # and the procedure(s) of Example # |
|---|---|---|---|---|---|---|---|---|
| 66 | single bond | O | H | H | H | H | CO$_2$H | 65/2, Step B |
| 67 | single bond | O | H | H | H | NO$_2$ | CO$_2$H | 65/3 |
| 68 | single bond | O | Cl | H | H | Cl | CO$_2$H | 65/4 |
| 69 | single bond | O | H | Cl | Cl | H | CO$_2$H | 65/5 |
| 70 | single bond | O | H | H | H | H | NHCO$_2$H | 65/6 |
| 71 | single bond | O | H | H | H | H | NHCO$_2$CH$_3$ | 70/7 |
| 72 | single bond | O | H | H | H | H | CN | 65/8 |
| 73 | single bond | O | H | H | H | H | 1H-tetrazol-5-yl | 72/9 |
| 74 | single bond | H, H | H | H | H | H | CN | 65/10 |
| 75 | single bond | H, H | H | H | H | H | 1H-tetrazol-5-yl | 74/11 |
| 76 | single bond | H, H | Cl | H | H | H | CN | 65/12 |
| 77 | single bond | H, H | Cl | H | H | H | 1H-tetrazol-5-yl | |

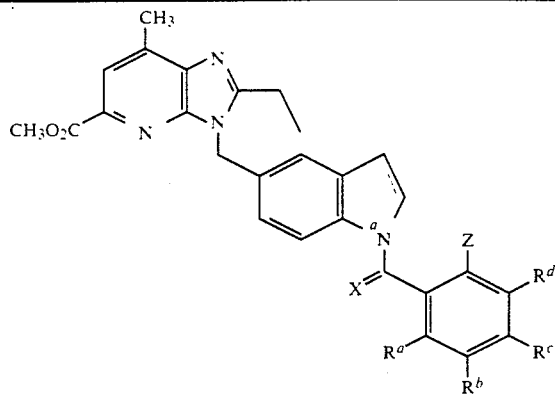

| # | a | X | $R^a$ | $R^b$ | $R^c$ | $R^d$ | Z | Utilizing the product of Example # and the procedure(s) of Example # |
|---|---|---|---|---|---|---|---|---|
| 76/13 | | | | | | | | |
| 78 | single bond | H. H | H | H | H | H | $CO_2CH_3$ | 65/14 |
| 79 | single bond | H. H | H | H | H | H | $CO_2H$ | 78/15 |
| 80 | single bond | H. H | H | Cl | Cl | H | $CO_2CH_3$ | 65/16 |
| 81 | single bond | H. H | H | Cl | Cl | H | $CO_2H$ | 80/15 |
| 82 | absent | O | H | H | H | H | CN | 65/17 |
| 83 | absent | O | H | H | H | H | 1H-tetrazol-5-yl | |
| 82/18 | | | | | | | | |
| 84 | absent | O | H | H | H | H | OC(=O)CH_3 | 82, Step A/19 |
| 85 | single bond | OH | H | H | H | H | OC(=O)CH_3 | 84/20 |
| 86 | absent | O | H | H | H | H | $CO_2H$ | 82, Step A/21 |
| 87 | absent | O | Cl | H | H | Cl | $CO_2H$ | 82, Step A/22 |
| 88 | absent | O | H | Cl | Cl | H | $CO_2H$ | 82, Step A/23 |
| 89 | absent | H. $CO_2CH_3$ | H | H | H | H | H | 82, Step A/24 |
| 90 | absent | H. $CO_2H$ | H | H | H | H | H | 89/25 |
| 91 | absent | H. CN | H | H | H | H | H | 82, Step A/26 |
| 92 | absent | H. CN | H | H | H | H | $CH_3$ | 82, Step A/27 |
| 93 | absent | H. CN | H | H | H | $CH_3$ | H | 82, Step A/28 |
| 94 | absent | H. CN | H | H | $CH_3$ | H | H | 82, Step A/29 |
| 95 | absent | H. 1H-tetrazol-5-yl | H | H | H | H | H | 91/30 |
| 96 | absent | H. 1H-tetrazol-5-yl | H | H | H | H | $CH_3$ | 92/30 |
| 97 | absent | H. 1H-tetrazol-5-yl | H | H | H | $CH_3$ | H | 93/30 |
| 98 | absent | H. 1H-tetrazol-5-yl | H | H | $CH_3$ | H | H | 94/30 |

EXAMPLE 100

3-(5-indolyl)methyl-2-propylbenzimidazole

Step A: Preparation of 2-Propylbenzimidazole

To a solution of o-phenylenediamine [obtained from the corresponding dihyrochloride (1.0 g, 5.52 mmols)] in methanol (30 ml) was added Cu(OAc)$_2$ (3.64 g, 18.2 mmols) as an aqueous solution (60 ml). After stirring for 10–15 min at room temperature, butyraldehyde (0.80 g, 11.1 mmols) was added and the mixture was heated at 100° C. for 4 h. Additional butyraldehyde (0.2 g) was added, and the mixture was stirred at room temerature overnight. The reaction was filtered and the residue was dissolved in methanol (40 ml). To this solution H$_2$S gas was bubbled for about 10 min followed by a stream of nitrogen. CuS was filtered-off, and the filtrate was evaporated in vacuo. The crude product was then purified by flash chromatography using ethyl acetate-hexane (3:1) to give the desired product (0.14 g, 16%).

NMR(CD$_3$OD): δ1.0(t, J=7 Hz, 3H), 1.88(m, 2H), 2.86(t, J=7 Hz, 2H), 7.2(m, 2H), 7.5(m, 2H); FAB-MS: m/e 161(M+H).

Step B: Preparation of 3-(5-indolyl)methyl-2-propylbenzimidazole

Following the procedures of Example 1, Steps D through F, followed by the procedure of Example 2, Step A the titled compound can be prepared.

EXAMPLE 101

2-butyl-3-[(5-indoly)methyl]benzimidazole

Step A: Preparation of 2-Butylbenzimidazole

To a solution of o-phenylenediamine (0.171 g, 1.58 mmol) in absolute ethanol (8 ml), ethyl valerylimidate (0.313 g, 1.9 mmol) was added, and the mixture was refluxed overnight. The reaction was cooled to room temperature and concentrated in vacuo. The residue was partitioned between ethyl acetate and saturated NaHCO$_3$. The organic phase was separated and the aqueous layer was extracted with ethyl acetate (3×20 ml). The organic layers were combined and washed with brine, dried (MgSO$_4$), and then concentrated in vacuo. The crude product, thus obtained, was purified by medium pressure liquid chromatography (MPLC) on silica-gel using ethyl acetate-hexane (1:1) to give cream colored crystalline solid (0.19 g, 69%).

NMR (CDCl$_3$): δ0.92 (t, J=7 Hz, 3H), 1.42(m, 2H), 1.86(m, 2H), 2.95(t, J=7 Hz, 2H), 7.22(m, 2H), 7.58(m, 2H); FAB-MS: m/e 174 (M+H).

Step B: Preparation of 2-butyl-3-[(5-indolyl)-methyl]-benzimidazole

Following the procedures of Example 1, Steps D through F, followed by the procedure of Example 2, Step A the titled compound can be prepared.

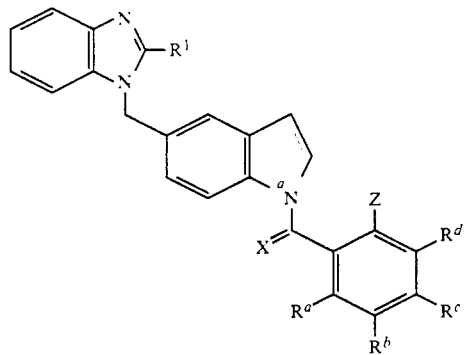

| # | R¹ | a | X | $R^a$ | $R^b$ | $R^c$ | $R^d$ | Z | Utilizing the product of Example # and the procedure(s) of Example # |
|---|---|---|---|---|---|---|---|---|---|
| 102 | propyl | single bond | O | H | H | H | H | $CO_2H$ | 100/2, Step B |
| 103 | propyl | single bond | O | H | H | H | $NO_2$ | $CO_2H$ | 100/3 |
| 104 | propyl | single bond | O | Cl | H | H | Cl | $CO_2H$ | 100/4 |
| 105 | propyl | single bond | O | H | Cl | Cl | H | $CO_2H$ | 100/5 |
| 106 | propyl | single bond | O | H | H | H | H | $NHCO_2H$ | 100/6 |
| 107 | propyl | single bond | O | H | H | H | H | $NHCO_2CH_3$ | 100/7 |
| 108 | propyl | single bond | O | H | H | H | H | CN | 100/8 |
| 109 | propyl | single bond | O | H | H | H | H | 1H-tetrazol-5-yl | 108/9 |
| 110 | propyl | single bond | H, H | H | H | H | H | CN | 100/10 |
| 111 | propyl | single bond | H, H | H | H | H | H | 1H-tetrazol-5-yl | 110/11 |
| 112 | propyl | single bond | H, H | Cl | H | H | H | CN | 100/12 |
| 113 | propyl | single bond | H, H | Cl | H | H | H | 1H-tetrazol-5-yl | 112/13 |
| 114 | propyl | single bond | H, H | H | H | H | H | $CO_2CH_3$ | 100/14 |
| 115 | propyl | single bond | H, H | H | H | H | H | $CO_2H$ | 114/15 |
| 116 | propyl | single bond | H, H | H | Cl | Cl | H | $CO_2CH_3$ | 100/16 |
| 117 | propyl | single bond | H, H | H | Cl | Cl | H | $CO_2H$ | 116/15 |
| 118 | propyl | absent | O | H | H | H | H | CN | 100/17 |
| 119 | propyl | absent | O | H | H | H | H | 1H-tetrazol-5-yl | 118/18 |
| 120 | propyl | absent | O | H | H | H | H | $OC(=O)CH_3$ | 118, Step A/19 |
| 121 | propyl | single bond | O | H | H | H | H | $OC(=O)CH_3$ | 120/20 |
| 122 | propyl | absent | O | H | H | H | H | $CO_2H$ | 118, Step A/21 |
| 123 | propyl | absent | O | Cl | H | H | Cl | $CO_2H$ | 118, Step A/22 |
| 124 | propyl | absent | O | H | Cl | Cl | H | $CO_2H$ | 118, Step A/23 |
| 125 | propyl | absent | H, $CO_2CH_3$ | H | H | H | H | H | 118, Step A/24 |
| 126 | propyl | absent | H, $CO_2H$ | H | H | H | H | H | 125/25 |
| 127 | propyl | absent | H, CN | H | H | H | H | H | 118, Step A/26 |
| 128 | propyl | absent | H, CN | H | H | H | H | $CH_3$ | 118, Step A/27 |
| 129 | propyl | absent | H, CN | H | H | H | $CH_3$ | H | 118, Step A/28 |
| 130 | propyl | absent | H, CN | H | H | $CH_3$ | H | H | 118, Step A/29 |
| 131 | propyl | absent | H, 1H-tetrazol-5-yl | H | H | H | H | H | 127/30 |
| 132 | propyl | absent | H, 1H-tetrazol-5-yl | H | H | H | H | $CH_3$ | 128/30 |
| 133 | propyl | absent | H, 1H-tetrazol-5-yl | H | H | H | $CH_3$ | H | 129/30 |
| 134 | propyl | absent | H, 1H-tetrazol-5-yl | H | H | $CH_3$ | H | H | 130/30 |
| 135 | n-butyl | single bond | O | H | H | H | H | $CO_2H$ | 101/2, Step B |
| 136 | n-butyl | single bond | O | H | H | H | $NO_2$ | $CO_2H$ | 101/3 |
| 137 | n-butyl | single bond | O | Cl | H | H | Cl | $CO_2H$ | 101/4 |
| 138 | n-butyl | single bond | O | H | Cl | Cl | H | $CO_2H$ | 101/5 |
| 139 | n-butyl | single bond | O | H | H | H | H | $NHCO_2H$ | 101/6 |
| 140 | n-butyl | single bond | O | H | H | H | H | $NHCO_2CH_3$ | 139/7 |
| 141 | n-butyl | single bond | O | H | H | H | H | CN | 101/8 |
| 142 | n-butyl | single bond | O | H | H | H | H | 1H-tetrazol-5-yl | 141/9 |
| 143 | n-butyl | single bond | H, H | H | H | H | H | CN | 101/10 |
| 144 | n-butyl | single bond | H, H | H | H | H | H | 1H-tetrazol-5-yl | 143/11 |
| 145 | n-butyl | single bond | H, H | Cl | H | H | H | CN | 101/12 |
| 146 | n-butyl | single bond | H, H | Cl | H | H | H | 1H-tetrazol-5-yl | 145/13 |
| 147 | n-butyl | single bond | H, H | H | H | H | H | $CO_2CH_3$ | 101/14 |
| 148 | n-butyl | single bond | H, H | H | H | H | H | $CO_2H$ | 147/15 |
| 149 | n-butyl | single bond | H, H | H | Cl | Cl | H | $CO_2CH_3$ | 101/16 |
| 150 | n-butyl | single bond | H, H | H | Cl | Cl | H | $CO_2H$ | 149/15 |
| 151 | n-butyl | absent | O | H | H | H | H | CN | 101/17 |
| 152 | n-butyl | absent | O | H | H | H | H | 1H-tetrazol-5-yl | 151/18 |
| 153 | n-butyl | absent | O | H | H | H | H | $OC(=O)CH_3$ | 151, Step A/19 |
| 154 | n-butyl | single bond | O | H | H | H | H | $OC(=O)CH_3$ | 153/20 |
| 155 | n-butyl | absent | O | H | H | H | H | $CO_2H$ | 151, Step A/21 |
| 156 | n-butyl | absent | O | Cl | H | H | Cl | $CO_2H$ | 151, Step A/22 |
| 157 | n-butyl | absent | O | H | Cl | Cl | H | $CO_2H$ | 151, Step A/23 |
| 158 | n-butyl | absent | H, $CO_2CH_3$ | H | H | H | H | H | 151, Step A/24 |
| 159 | n-butyl | absent | H, $CO_2H$ | H | H | H | H | H | 158/25 |
| 160 | n-butyl | absent | H, CN | H | H | H | H | H | 151, Step A/26 |
| 161 | n-butyl | absent | H, CN | H | H | H | H | $CH_3$ | 151, Step A/27 |

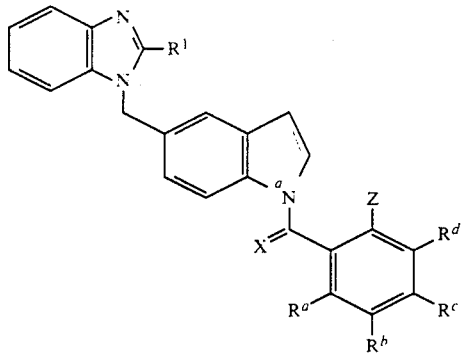

| # | R¹ | a | X | Rᵃ | Rᵇ | Rᶜ | Rᵈ | Z | Utilizing the product of Example # and the procedure(s) of Example # |
|---|----|---|---|----|----|----|----|---|---|
| 162 | n-butyl | absent | H, CN | H | H | H | CH₃ | H | 151, Step A/28 |
| 163 | n-butyl | absent | H, CN | H | H | CH₃ | H | H | 151, Step A/29 |
| 164 | n-butyl | absent | H, 1H-tetrazol-5-yl | H | H | H | H | H | 160/30 |
| 165 | n-butyl | absent | H, 1H-tetrazol-5-yl | H | H | H | H | CH₃ | 161/30 |
| 166 | n-butyl | absent | H, 1H-tetrazol-5-yl | H | H | H | CH₃ | H | 162/30 |
| 167 | n-butyl | absent | H, 1H-tetrazol-5-yl | H | H | CH₃ | H | H | 163/30 |

EXAMPLE 168

Preparation of 2-Chloro-6-methyl-8-propyl-9-(2'-(tetrazol-5-yl)biphen-4-yl)methylpurine Step A: 2-Chloro-6-methyl-8-propylpurine A mixture of 2-Chloro-4, 5-dimamino-6-methylpyrimidine (0.80 g, 5.04 mmol), trimethylorthobutyrate (1.2 ml, 7.6 mmol) and p-TsOH (0.08 g) in 2-methoxyethanol (24 ml) was heated in an oil bath at 140° C. for 24 hours, and then concentrated in vacuo. The residue was partitioned between water and ethyl acetate. The organic phase was then washed with brine and dried over MgSO₄. The crude product obtained after evaporation of the solvent was purified by flash chromatography using EtOAc-hexane (1:1) to give the crystalline titled compound (0.5 g, 47%).

NMR (CDCl₃): δ1.03 (t, J=8Hz, 3H), 1.9 (q, 2HO, 2.82 (s, 3H), 3.0 (t, J=8Hz, 2H). FAB-MS: m/e 211 and 213 (M+H).

Analysis calculated for C₉H₁₁N₄Cl: C, 51.31; H, 5.26; N, 26.60. Found: C, 51.43; H, 5.50, N, 26.81.

EXAMPLE 169

Preparation of 2-Dimethylamino-6-methyl-8-propyl-9-(2'-(tetrazol-5-yl)-biphen-4-yl)methylpurine Step A: 2-Dimethylamino-6-methyl-8-propylpurine To a solution of 2-Chloro-6-methyl-8-propylpurine (from Example 168) (0.1 g, 0.47 mmol) in ethanol (2 ml) was added condensed dimethylamine (1 ml) at 0° C. The mixture was then placed in a steel-bomb and heated at 110° C. for 7 hours. The reaction was cooled and the mixture was concentrated in vacuo. The residue was partitioned between CHCl and water, and the organic was separated and dried over MgSO₄. The crude product obtained after removal of the solvent was purified by flash-chromatography on silica-gel using 5% MeOH in CHCl₃ giving the titled compound as an amorphous solid (0.065 g, 64%).

NMR (CDCl₃): δ1.01 (t, J=8Hz, 3H), 1.8 (q, J=8Hz, 2H), 2.65 (s, 3H), 2.8 (t, J=8Hz, 2H), 3.2 (s, 6H).

FAB-MS: m/e 220 (M+H).

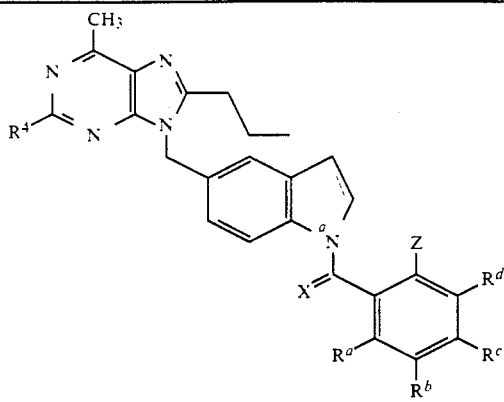

| # | $R^4$ | a | X | $R^a$ | $R^b$ | $R^c$ | $R^d$ | Z | Utilizing the product of Example # and the procedure(s) of Example # |
|---|---|---|---|---|---|---|---|---|---|
| 170 | Cl | single bond | O | H | H | H | H | $CO_2H$ | 168/2, Step B |
| 171 | Cl | single bond | O | H | H | H | $NO_2$ | $CO_2H$ | 168/3 |
| 172 | Cl | single bond | O | Cl | H | H | Cl | $CO_2H$ | 168/4 |
| 173 | Cl | single bond | O | H | Cl | Cl | H | $CO_2H$ | 168/5 |
| 174 | Cl | single bond | O | H | H | H | H | $NHCO_2H$ | 168/6 |
| 175 | Cl | single bond | O | H | H | H | H | $NHCO_2CH_3$ | 174/7 |
| 176 | Cl | single bond | O | H | H | H | H | CN | 168/8 |
| 177 | Cl | single bond | O | H | H | H | H | 1H-tetrazol-5-yl | 176/9 |
| 178 | Cl | single bond | H, H | H | H | H | H | CN | 168/10 |
| 179 | Cl | single bond | H, H | H | H | H | H | 1H-tetrazol-5-yl | 178/11 |
| 180 | Cl | single bond | H, H | Cl | H | H | H | CN | 168/12 |
| 181 | Cl | single bond | H, H | Cl | H | H | H | 1H-tetrazol-5-yl | 180/13 |
| 182 | Cl | single bond | H, H | H | H | H | H | $CO_2CH_3$ | 168/14 |
| 183 | Cl | single bond | H, H | H | H | H | H | $CO_2H$ | 182/15 |
| 184 | Cl | single bond | H, H | H | Cl | Cl | H | $CO_2CH_3$ | 168/16 |
| 185 | Cl | single bond | H, H | H | Cl | Cl | H | $CO_2H$ | 184/15 |
| 186 | Cl | absent | O | H | H | H | H | CN | 168/17 |
| 187 | Cl | absent | O | H | H | H | H | 1H-tetrazol-5-yl | 186/18 |
| 188 | Cl | absent | O | H | H | H | H | $OC(=O)CH_3$ | 186, Step A/19 |
| 189 | Cl | single bond | O | H | H | H | H | $OC(=O)CH_3$ | 188/20 |
| 190 | Cl | absent | O | H | H | H | H | $CO_2H$ | 186, Step A/21 |
| 191 | Cl | absent | O | Cl | H | H | Cl | $CO_2H$ | 186, Step A/22 |
| 192 | Cl | absent | O | H | Cl | Cl | H | $CO_2H$ | 186, Step A/23 |
| 193 | Cl | absent | H, $CO_2CH_3$ | H | H | H | H | H | 186, Step A/24 |
| 194 | Cl | absent | H, $CO_2H$ | H | H | H | H | H | 193/25 |
| 195 | Cl | absent | H, CN | H | H | H | H | H | 186, Step A/26 |
| 196 | Cl | absent | H, CN | H | H | H | H | $CH_3$ | 186, Step A/27 |
| 197 | Cl | absent | H, CN | H | H | H | $CH_3$ | H | 186, Step A/28 |
| 198 | Cl | absent | H, CN | H | H | $CH_3$ | H | H | 186, Step A/29 |
| 199 | Cl | absent | H, 1H-tetrazol-5-yl | H | H | H | H | H | 195/30 |
| 200 | Cl | absent | H, 1H-tetrazol-5-yl | H | H | H | H | $CH_3$ | 196/30 |
| 201 | Cl | absent | H, 1H-tetrazol-5-yl | H | H | H | $CH_3$ | H | 197/30 |
| 202 | Cl | absent | H, 1H-tetrazol-5-yl | H | H | $CH_3$ | H | H | 198/30 |
| 203 | $N(CH_3)_2$ | single bond | O | H | H | H | H | $CO_2H$ | 169/2, Step B |
| 204 | $N(CH_3)_2$ | single bond | O | H | H | H | $NO_2$ | $CO_2H$ | 169/3 |
| 205 | $N(CH_3)_2$ | single bond | O | Cl | H | H | Cl | $CO_2H$ | 169/4 |
| 206 | $N(CH_3)_2$ | single bond | O | H | Cl | Cl | H | $CO_2H$ | 169/5 |
| 207 | $N(CH_3)_2$ | single bond | O | H | H | H | H | $NHCO_2H$ | 169/6 |
| 208 | $N(CH_3)_2$ | single bond | O | H | H | H | H | $NHCO_2CH_3$ | 207/7 |
| 209 | $N(CH_3)_2$ | single bond | O | H | H | H | H | CN | 168/8 |
| 210 | $N(CH_3)_2$ | single bond | O | H | H | H | H | 1H-tetrazol-5-yl | 209/9 |
| 211 | $N(CH_3)_2$ | single bond | H, H | H | H | H | H | CN | 169/10 |
| 212 | $N(CH_3)_2$ | single bond | H, H | H | H | H | H | 1H-tetrazol-5-yl | 211/11 |
| 213 | $N(CH_3)_2$ | single bond | H, H | Cl | H | H | H | CN | 169/12 |
| 214 | $N(CH_3)_2$ | single bond | H, H | Cl | H | H | H | 1H-tetrazol-5-yl | 213/13 |
| 215 | $N(CH_3)_2$ | single bond | H, H | H | H | H | H | $CO_2CH_3$ | 169/14 |
| 216 | $N(CH_3)_2$ | single bond | H, H | H | H | H | H | $CO_2H$ | 215/15 |
| 217 | $N(CH_3)_2$ | single bond | H, H | H | Cl | Cl | H | $CO_2CH_3$ | 169/16 |
| 218 | $N(CH_3)_2$ | single bond | H, H | H | Cl | Cl | H | $CO_2H$ | 217/15 |
| 219 | $N(CH_3)_2$ | absent | O | H | H | H | H | CN | 169/17 |
| 220 | $N(CH_3)_2$ | absent | O | H | H | H | H | 1H-tetrazol-5-yl | 219/18 |
| 221 | $N(CH_3)_2$ | absent | O | H | H | H | H | $OC(=O)CH_3$ | 219, Step A/19 |
| 222 | $N(CH_3)_2$ | single bond | O | H | H | H | H | $OC(=O)CH_3$ | 221/20 |
| 223 | $N(CH_3)_2$ | absent | O | H | H | H | H | $CO_2H$ | 219, Step A/21 |
| 224 | $N(CH_3)_2$ | absent | O | Cl | H | H | Cl | $CO_2H$ | 219, Step A/22 |
| 225 | $N(CH_3)_2$ | absent | O | H | Cl | Cl | H | $CO_2H$ | 219, Step A/23 |
| 226 | $N(CH_3)_2$ | absent | H, $CO_2CH_3$ | H | H | H | H | H | 219, Step A/24 |
| 227 | $N(CH_3)_2$ | absent | H, $CO_2H$ | H | H | H | H | H | 226/25 |
| 228 | $N(CH_3)_2$ | absent | H, CN | H | H | H | H | H | 219, Step A/26 |

-continued

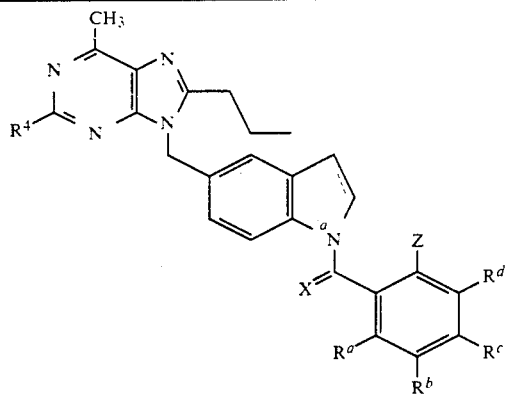

| # | R⁴ | a | X | Rᵃ | Rᵇ | Rᶜ | Rᵈ | Z | Utilizing the product of Example # and the procedure(s) of Example # |
|---|---|---|---|---|---|---|---|---|---|
| 229 | N(CH₃)₂ | absent | H, CN | H | H | H | H | CH₃ | 219, Step A/27 |
| 230 | N(CH₃)₂ | absent | H, CN | H | H | H | CH₃ | H | 219, Step A/28 |
| 231 | N(CH₃)₂ | absent | H, CN | H | H | CH₃ | H | H | 219, Step A/29 |
| 232 | N(CH₃)₂ | absent | H, 1H-tetrazol-5-yl | H | H | H | H | H | 228/30 |
| 233 | N(CH₃)₂ | absent | H, 1H-tetrazol-5-yl | H | H | H | H | CH₃ | 229/30 |
| 234 | N(CH₃)₂ | absent | H, 1H-tetrazol-5-yl | H | H | H | CH₃ | H | 230/30 |
| 235 | N(CH₃)₂ | absent | H, 1H-tetrazol-5-yl | H | H | CH₃ | H | H | 231/30 |

What is claimed is:

1. A compound of structural formula I or a pharmaceutically acceptable salt

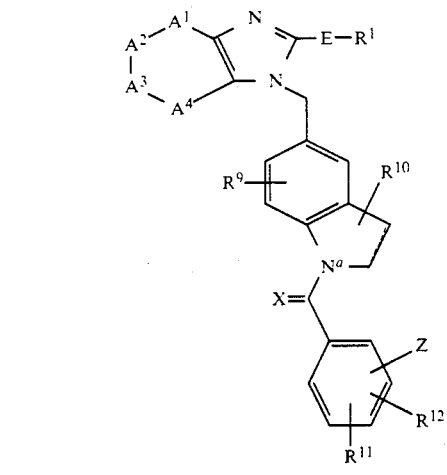

wherein:

R¹ is:
(a) (C₁–C₆)-alkyl, (C₂–C₆)-alkenyl or (C₂–C₆)-alkynyl each of which can be unsubstituted or substituted with a substituent selected from the group consisting of:
  i) aryl as defined below in R¹(b),
  ii) (C₃–C₇)-cycloalkyl,
  iii) Cl, Br, I, F,
  iv) OH,
  v) NH₂,
  vi) NH(C₁–C₄)-alkyl,
  vii) N[((C₁–C₄)-alkyl)]₂,
  viii) NHSO₂R²,
  ix) CF₃,
  x) COOR², or
  xi) SO₂NHR²ᵃ;

(b) aryl, wherein aryl is defined as phenyl or naphthyl, unsubstituted or substituted with 1 or 2 substituents selected form the group consisting of:
  i) Cl, Br, I, F,
  ii) (C₁–C₄)-alkyl,
  iii) (C₁–C₄)-alkoxy,
  iv) NO₂
  v) CF₃,
  vi) SO₂NR²ᵃR²ᵃ,
  vii) (C₁–C₄)-alkylthio,
  viii) hydroxy,
  ix) amino,
  x) (C₃–C₇)-cycloalkyl, or
  xi) (C₃–C₁₀)-alkenyl, (c) heteroaryl, wherein heteroaryl is defined as a 5- or 6-membered heteroaromatic moiety, which can contain one or two members selected from the group consisting of N, O, S and wherein the heteroaryl is optionally mono- or disubstituted with substituents selected from the group consisting of:
  i) Cl, Br, I, F,
  ii) OH,
  iii) SH,
  iv) NO₂,
  v) (C₁–C₄)-alkyl,
  vi) (C₂–C₄)-alkenyl,
  vii) (C₂–C₄)-alkynyl,
  viii) (C₁–C₄)-alkoxy, or
  ix) CF₃, (d) (C₁–C₄)-perfluoroalkyl,
(e) (C₃–C₈)-cycloalkyl, or
(f) (C₁–C₄)-alkyl-(C₃–C₈)-cycloalkyl;

—A¹—A²—A³—A⁴— is:
(a)

(b) 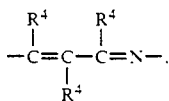

(c) 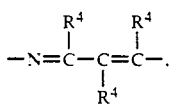

(d) 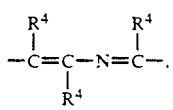

(e) 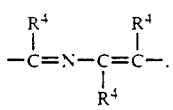

(f) 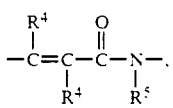

(g) 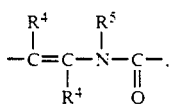

(h) 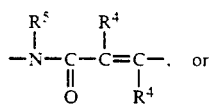 or

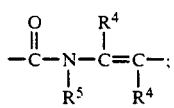

E is:
(a) a single bond,
(b) —S(O)$_n$(CH$_2$)$_s$—, or
(c) —O—;
n is 0 to 2;
s is 0 to 5;
a is a single bond or absent;
X is
(a) O,
(b) H; H,
(c) H; CO$_2$-(C$_1$–C$_4$)-alkyl,
(d) H; CO$_2$H,
(e) H; CN,
(f) H; 1H-tetrazol-5-yl, or
(g) H; CONHSO$_2$R$^{14}$;

R$^2$ is:
(a) H, or
(b) (C$_1$–C$_6$)-alkyl;

R$^{2a}$ is:
(a) R$^2$,
(b) CH$_2$-aryl
(c) aryl;

R$^4$ groups are independently:
(a) H,
(b) (C$_1$–C$_6$)-alkyl, (C$_2$–C$_6$)-alkenyl, or (C$_2$–C$_6$)-alkynyl, each of which is unsubstituted or substituted with:
  i) OH,
  ii) (C$_1$–C$_4$)-alkoxy,
  iii) CO$_2$R$^2$,
  iv) OCOR$^2$,
  v) CONHR$^2$,
  vi) CON(R$^2$)$_2$,
  vii) N(R$^2$)C(=O)R$^2$,
  viii) NH$_2$,
  ix) (C$_1$–C$_4$)-alkylamino,
  x) di[(C$_1$–C$_4$)-alkyl]amino,
  xi) aryl,
  xii) heteroaryl, wherein heteroaryl is as defined in R$^1$ (c),
(c) —C(=O)-aryl,
(d) (C$_3$–C$_7$)-cycloalkyl,
(e) Cl, Br, I, F,
(f) —OH,
(g) —OR$^{21}$,
(h) —CF$_3$,
(i) —SH,
(j) —S(O)$_n$—(C$_1$–C$_4$)-alkyl,
(k) —CO$_2$R$^{2a}$,
(l) —SO$_3$H,
(m) —NR$^2$R$^{21}$,
(n) —NR$^2$C(=O)R$^{21}$,
(o) —NR$^2$COOR$^{21}$,
(p) —SO$_2$NHR$^{21}$,
(q) —SO$_2$NR$^2$R$^{2a}$,
(r) —NO$_2$,
(s) —NHSO$_2$—(C$_1$–C$_4$)—alkyl,
(t) —C(O)NHSO$_2$R$^{14}$,
(u) aryl,
(v) heteroaryl, wherein heteroaryl is as defined in R$^1$ (c), or
(w) morpholin-4-yl;

R$^5$ is:
(a) H, or
(b) (C$_1$–C$_6$)-alkyl or (C$_2$–C$_6$)-alkenyl, unsubstituted or substituted with:
  i) hydroxy, or
  ii) (C$_1$–C$_4$)-alkoxy;

R$^9$ and R$^{10}$ are each independently:
(a) H,
(b) Cl, Br, I, F,
(c) NO$_2$,
(d) (C$_1$–C$_6$)-alkyl,
(e) (C$_1$–C$_6$)-acyloxy,
(f) (C$_3$–C$_6$)-cycloalkyl,
(g) (C$_1$–C$_6$)-alkoxy,
(h) —NHSO$_2$R$^{2a}$,
(i) hydroxy-(C$_1$–C$_4$)-alkyl, (j) aryl-$(C_1-C_4)$-alkyl,
(k) $(C_1-C_4)$-alkylthio,
(l) $(C_1-C_4)$-alkylsulfinyl,
(m) $(C_1-C_4)$-alkylsulfonyl,
(n) $NH_2$,
(o) $NH[(C_1-C_4)$-alkyl],
(p) $N[(C_1-C_4)$-alkyl]$_2$,
(q) $CF_3$,
(r) $-SO_2-NHR^{2a}$,
(s) furyl, or
(t) aryl, wherein aryl is phenyl or naphthyl unsubstituted or substituted with one or two substituents selected from the group consisting of: Cl, Br, I, F, $(C_1-C_4)$-alkyl, $(C_1-C_4)$-alkoxy, $NO_2$, $CF_3$, $(C_1-C_4)$-alkylthio, OH, $NH_2$, $-NH[(C_1-C_4)$-alkyl], $-N[(C_1-C_4)$-alkyl]$_2$, $-CO_2H$, or $-CO_2-(C_1-C_4)$-alkyl;
(u) when $R^9$ and $R^{10}$ are bonded to adjacent carbon atoms, they can be joined to form an aryl ring;

$R^{11}$ and $R^{12}$ are independently:
(a) H,
(b) Cl, Br, I, F,
(c) $NO_2$,
(d) $NH_2$,
(e) $NH[(C_1-C_4)$-alkyl],
(f) $N[(C_1-C_4)$-alkyl]$_2$,
(g) $SO_2NHR^{2a}$,
(h) $CF_3$,
(i) $(C_1-C_4)$-alkyl,
(j) $(C_1-C_4)$-alkoxy, or
(k) when $R^{11}$ and $R^{12}$ are bonded to adjacent carbon atoms, they can be joined to form an aryl ring;

Z is:
(a) $-H$,
(b) $-CO_2R^{2a}$,
(c) $-SO_3R^{13}$,
(d) $-NHSO_2CF_3$,
(e) $-PO(OR^{13})_2$,
(f) $-SO_2NHR^{14}$,
(g) $-CONHOR^{13}$, or
(h) $-CR^{2a}(OH)PO(OR^{13})_2$;
(i) $-CN$,
(j) $-SO_2NH$-heteroaryl, wherein heteroaryl is as defined in $R^1$ (c) above,
(k) $-CH_2SO_2NH$-heteroaryl, wherein heteroaryl is as defined in $R^1$ (c) above,
(l) $-SO_2NH-CO-R^{14}$,
(m) $-CH_2SO_2NH-CO-R^{14}$,
(n) $-CONH-SO_2R^{14}$,
(o) $-CH_2CONH-SO_2R^{14}$,
(p) $-NHSO_2NHCO-R^{14}$,
(q) $-NHCONHSO_2-R^{14}$,
(r) $-NHCO_2R^{2a}$,
(s)

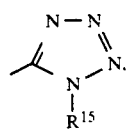

(t)

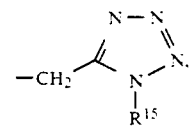

(u)

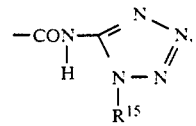

(v) $-CONHNHSO_2CF_3$,
(w)

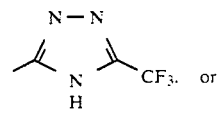

or (x)

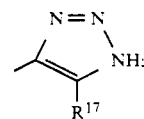

$R^{13}$ is H, or $-CH(R^4)-O-C(O)R^4$;
$R^{14}$ is
(a) aryl,
(b) heteroaryl, wherein heteroaryl is as defined in $R^1$ (c),
(c) $(C_3-C_7)$-cycloalkyl,
(d) $(C_1-C_4)$-alkyl unsubstituted or substituted with a substituent selected from the group consisting of aryl, heteroaryl, wherein heteroaryl is as defined in $R^1$ (c), $-OH$, $-SH$, $(C_1-C_4)$-alkyl, $-O(C_1-C_4)$-alkyl, $-S(C_1-C_4)$-alkyl, $-CF_3$, Cl, Br, F, I, $-NO_2$, $-CO_2H$, $CO_2$-$(C_1-C_4)$-alkyl, $-NH_2$, $-NH[(C_1-C_4)$-alkyl]$_2$, $-PO_3H$, $PO(OH)$ $(O-(C_1-C_4)$-alkyl);

$R^{15}$ is H, $(C_1-C_6)$-alkyl, $(C_2-C_4)$-alkenyl, $(C_1-C_4)$-alkoxy alkyl, or benzyl, wherein the phenyl is unsubstituted or substituted with a substituent selected from the group consisting of: $-NO_2$, $-NH_2$, $-OH$ or $-OCH_3$;

$R^{17}$ is $-CN$, $-NO_2$, $-CO_2R^{2a}$, or $-CF_3$; and $R^{21}$ is:
(a) H, or
(b) $(C_1-C_4)$-alkyl unsubstituted or substituted with:
i) $NH_2$,
ii) $NH[(C_1-C_4)$-alkyl],
iii) $N[(C_1-C_4)$-alkyl]$_2$,
iv) $CO_2H$,
v) $CO_2(C_1-C_4)$-alkyl,
vi) OH,
vii) $SO_3H$, or
viii) $SO_2NH_2$.

2. The compound of claim 1 wherein:
$R^1$ is:
(a) $(C_1-C_6)$-alkyl, $(C_2-C_6)$-alkenyl or $(C_2-C_6)$-alkynyl each of which can be unsubstituted or substituted with a substituent selected from the group consisting of:
i) aryl,
ii) $(C_3-C_7)$-cycloalkyl,
iii) Cl, Br, I, F,
iv) OH,
v) $NH_2$,
vi) $NH(C_1-C_4)$-alkyl,
vii) $N[((C_1-C_4)\text{-alkyl})]_2$,
viii) $NHSO_2R^2$,
ix) $CF_3$,
x) $COOR^2$, or
xi) $SO_2NHR^{2a}$,
(b) $(C_1-C_4)$-perfluoroalkyl,
(c) $(C_3-C_8)$-cycloalkyl, or
(d) $(C_1-C_4)$-alkyl-$(C_3-C_8)$-cycloalkyl;

—$A^1$—$A^2$—$A^3$—$A^4$— is:

(a)

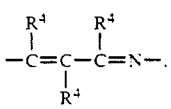

(b)

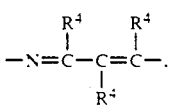

(c)

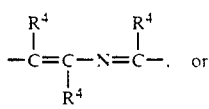

(d)

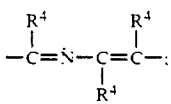

E is: a single bond;
n is 0 to 2;
a is a single bond or absent;
X is
(a) O,
(b) H; H,
(c) H; $CO_2$-$(C_1-C_4)$-alkyl,
(d) H; $CO_2H$,
(e) H; CN,
(f) H; 1H-tetrazol-5-yl, or
(g) H; $CONHSO_2R^{14}$;

$R^2$ is:
(a) H, or
(b) $(C_1-C_6)$-alkyl;

$R^{2a}$ is:
(a) $R^2$,
(b) $CH_2$-aryl
(c) aryl;

$R^4$ groups are independently:
(a) H,
(b) $(C_1-C_6)$-alkyl, $(C_2-C_6)$-alkenyl, $(C_2-C_6)$-alkynyl or $(C_3-C_8)$-cycloalkyl, each of which is unsubstituted or substituted with:
   i) OH,
   ii) $(C_1-C_4)$-alkoxy,
   iii) $CO_2R^2$,
   iv) $OCOR^2$,
   v) $CONHR^2$,
   vi) $CON(R^2)_2$,
   vii) $N(R^2)C(O)R^2$,
   viii) $NH_2$,
   ix) $(C_1-C_4)$-alkylamino,
   x) di$[(C_1-C_4)$-alkyl]amino,
   xi) aryl,
   xii) heteroaryl,
(c) —C(O)—aryl,
(d) —$NO_2$,
(e) Cl, Br, I, F,
(f) —OH,
(g) —$OR^{21}$,
(h) —$CF_3$,
(i) —SH,
(j) —$S(O)_n$—$(C_1-C_4)$-alkyl,
(k) —$CO_2R^2$,
(l) —$SO_3H$,
(m) —$NR^2R^{21}$,
(n) —$NR^2C(O)R^{21}$,
(o) —$NR^2COOR^{21}$,
(p) —$SO_2NHR^{21}$,
(q) —$SO_2NR^2R^{2a}$,
(r) —$NHSO_2R^{14}$,
(s) —$C(O)NHSO_2R^{14}$,
(t) aryl,
(u) heteroaryl, or
(v) morpholin-4-yl;

$R^5$ is:
(a) H, or
(b) $(C_1-C_6)$-alkyl or $(C_2-C_6)$-alkenyl, unsubstituted or substituted with:
   i) hydroxy, or
   ii) $(C_1-C_4)$-alkoxy;

$R^9$ and $R^{10}$ are each independently:
(a) H,
(b) Cl, Br, I, F,
(c) $NO_2$,
(d) $(C_1-C_6)$-alkyl,
(e) $(C_1-C_6)$-alkoxy,
(f) $CF_3$,
(g) $NH_2$,
(h) $NH[(C_1-C_4)$-alkyl],
(i) $N[(C_1-C_4)$-alkyl]$_2$,
(j) $CF_3$,
(k) when $R^9$ and $R^{10}$ are bonded to adjacent carbon atoms, they can be joined to form an aryl ring;

$R^{11}$ and $R^{12}$ are independently:
(a) H,
(b) Cl, Br, I, F,
(c) $NO_2$,
(d) $NH_2$,
(e) $NH[(C_1-C_4)$-alkyl],
(f) $N[(C_1-C_4)$-alkyl]$_2$,
(g) $SO_2NHR^{2a}$,
(h) $CF_3$,
(i) $(C_1-C_4)$-alkyl,
(j) $(C_1-C_4)$-alkoxy, or
(k) when $R^{11}$ and $R^{12}$ are bonded to adjacent carbon atoms, they can be joined to form an aryl ring;

Z is:
- (a) —H,
- (b) —CO$_2$R$^{2a}$,
- (c) —SO$_3$R$^{13}$,
- (d) —NHSO$_2$CF$_3$,
- (e) —SO$_2$NHR$^{14}$,
- (f) —CONHOR$^{13}$,
- (g) —CONH-1H-tetrazol-5-yl,
- (h) -1H-tetrazol-5-yl,
- (i) CF$_3$,
- (j) SO2NH-heteroaryl,
- (k) —CH$_2$SO$_2$NH-heteroaryl,
- (l) —SO$_2$NH—CO—R$^{14}$,
- (m) —CH$_2$SO$_2$NH—CO—R$^{14}$,
- (n) —CONH—SO$_2$R$^{14}$,
- (o) —CH$_2$CONH—SO$_2$R$^{14}$,
- (p) —NHSO$_2$NHCO—R$^{14}$,
- (q) —NHCONHSO$_2$—R$^{14}$, or
- (r) —NHCO$_2$R$^{2a}$;

R$^{14}$ is
- (a) aryl,
- (b) heteroaryl,
- (c) (C$_3$-C$_7$)-cycloalkyl,
- (d) (C$_1$-C$_4$)-alkyl unsubstituted or substituted with a substituent selected from the group consisting of aryl, heteroaryl, —OH, —SH, (C$_1$-C$_4$)-alkyl, —O(C$_1$-C$_4$)-alkyl, —S(C$_1$-C$_4$)-alkyl, —CF$_3$, Cl, Br, F, I, —NO$_2$, —CO$_2$H, CO$_2$-(C$_1$-C$_4$)-alkyl, —NH$_2$, —NH[(C$_1$-C$_4$)-alkyl]$_2$, —PO$_3$H, PO(OH) (O-(C$_1$-C$_4$)-alkyl);

R$^{15}$ is H, (C$_1$-C$_6$)-alkyl, (C$_2$-C$_4$)-alkenyl, (C$_1$-C$_4$)-alkoxy alkyl, or benzyl, wherein the phenyl is unsubstituted or substituted with a substituent selected from the group consisting of: —NO$_2$, —NH$_2$, —OH or —OCH$_3$;

R$^{21}$ is:
- (a) H, or
- (b) (C$_1$-C$_4$)-alkyl unsubstituted or substituted with:
  - i) NH$_2$,
  - ii) NH[(C$_1$-C$_4$)-alkyl],
  - iii) N[(C$_1$-C$_4$)-alkyl]$_2$,
  - iv) CO$_2$H,
  - v) CO$_2$(C$_1$-C$_4$)-alkyl,
  - vi) OH,
  - vii) SO$_3$H, or
  - viii) SO$_2$NH$_2$.

3. A compound selected from the group consisting of:
3-[N-(2-carboxy-3,6-dichlorobenzoyl)-5-indolyl]methyl-5,7-dimethyl-2-ethyl-3H-imidazo[4,5-b]pyridine;
3-[N-(2-carboxy-4,5-dichlorobenzoyl)-5-indolyl]methyl-5,7-dimethyl-2-ethyl-3H-imidazo[4,5-b]pyridine;
3-[N-(2-tetrazol-5-yl-benzoyl)-5-indolyl]methyl-5,7-dimethyl-2-ethyl-3H-imidazo[4,5-b]pyridine;
3-[N-(2-tetrazol-5-yl-6-Chlorobenzyl)-5-indolyl]methyl-5,7-dimethyl-2-ethyl-3H-imidazo[4,5-b]pyridine;
3-[N-(1-carboxy-1-phenyl)methyl-5-dihydroindolyl]methyl-5,7-dimethyl-2-ethyl-3H-imidazo[4,5-b]pyridine; or
3-[N-(1-tetrazol-5-yl-1-phenyl)methyl-5-dihydroindolyl]methyl-5,7-dimethyl-2-ethyl-3H-imidazo[4,5-b]pyridine.

4. The compound of claim 1 in which the structural formula is

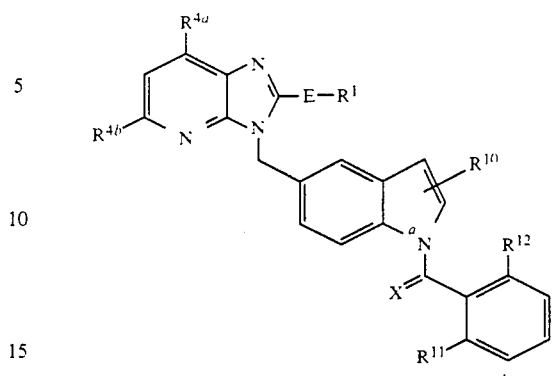

wherein:
R$^1$ is:
- a) (C$_1$-C$_6$)-alkyl,
- b) (C$_3$-C$_8$)-cycloalkyl, or
- c) (C$_1$-C$_4$)-alkyl-(C$_3$-C$_8$)-cycloalkyl;

E is: single bond, O, or S;

R$^{4a}$ is:
- (a) H,
- (b) (C$_1$-C$_4$)-alkyl,
- (c) (C$_1$-C$_4$)-perfluoroalkyl,
- (d) (C$_1$-C$_3$)-alkoxyl,
- (e) (C$_1$-C$_3$)-alkylthio,
- (f) (C$_3$-C$_8$)-cycloalkyl, or
- (g) F, Cl;

R$^{4b}$ is:
- (a) R$^{4a}$,
- (b) (C$_1$-C$_6$)-alkyl, (C$_2$-C$_6$)-alkenyl, substituted with a substituent selected from the group consisting of:
  - i) CO$_2$R$^2$,
  - ii) aryl, or
  - iii) heteroaryl,
- (c) —OH,
- (d) —CF$_3$,
- (e) —CO$_2$R$^2$,
- (f) —NR$^2$R$^2$,
- (g) —CO$_2$NH$_2$,
- (h) —CONHSO$_2$R$^{14}$,
- (i) 1H-tetrazol-5-yl,
- (j) aryl,
- (k) heteroaryl, or
- (l) morpholin-4-yl;

X is:
- (a) H; CO$_2$(C$_1$-C$_4$)-alkyl,
- (b) H; CO$_2$H,
- (c) H; CN,
- (d) H; 1H-tetrazol-5-yl, or
- (e) H; CONHSO$_2$R$^{14}$;

R$^{10}$ is: H or (C$_1$-C$_3$)-alkyl; and

R$^{11}$ and R$^{12}$ are independently:
H,
CH$_3$,
Cl,
Br,
OCH$_3$, or
CF$_3$.

5. The compound of claim 1 in which the structural formula is

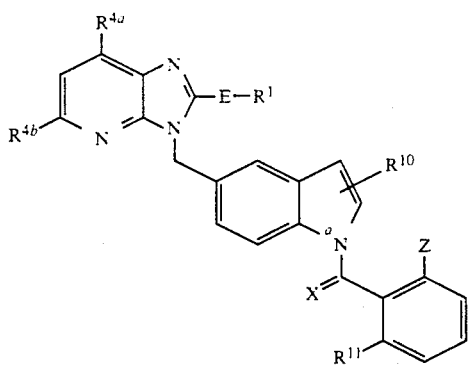

wherein:

R¹ is:
a) $(C_1-C_6)$-alkyl,
b) $(C_3-C_8)$-cycloalkyl, or
c) $(C_1-C_4)$-alkyl-$(C_3-C_8)$-cycloalkyl;

E is: single bond, O, or S;

$R^{4a}$ is:
(a) H,
(b) $(C_1-C_4)$-alkyl,
(c) $(C_1-C_4)$-perfluoroalkyl,
(d) $(C_1-C_3)$-alkoxyl,
(e) $(C_1-C_3)$-alkylthio,
(f) $(C_3-C_8)$-cycloalkyl, or
(g) F, Cl;

$R^{4b}$ is:
(a) $R^{4a}$,
(b) $(C_1-C_6)$-alkyl, $(C_2-C_6)$-alkenyl, substituted with a substituent selected from the group consisting of:
  i) $CO_2R^2$,
  ii) aryl, or
  iii) heteroaryl,
(c) —OH,
(d) —CF₃,
(e) —CO₂R²,
(f) —NR²R²,
(g) —CO₂NH₂,
(h) —CONHSO₂R¹⁴,
(i) 1H-tetrazol-5-yl,
(j) aryl,
(k) heteroaryl, or
(l) morpholin-4-yl;

X is:
(a) O, or
(b) H; H;

$R^{10}$ is: H or $(C_1-C_3)$-alkyl;

$R^{11}$ is:
H,
CH₃,
Cl,
Br,
OCH₃, or
CF₃; and

Z is: —CO₂R²ᵃ, —SO₂NHR¹⁴, or —1H-tetrazol-5-yl.

6. A pharmaceutical composition useful in the treatment of hypertension which comprises a pharmaceutically acceptable carrier and a therapeutically effective amount of a compound of claim 1.

7. A method of treating hypertension which comprises administering to a patient in need of such treatment a therapeutically effective amount of a compound of claim 1.

8. An ophthalmological formulation for the treatment of ocular hypertension comprising an ophthalmologically acceptable carrier and an effective ocular antihypertensive amount of a compound of claim 1.

9. A method of treating ocular hypertension comprising topical ocular administration to a patient in need of such treatment of an effective ocular antihypertensive amount of a compound of claim 1.

10. A method of treating cognitive dysfunction, anxiety, or depression comprising administering to a patient in need of such treatment, a therapeutically effective amount of a compound of claim 1.

* * * * *

UNITED STATES PATENT AND TRADEMARK OFFICE
CERTIFICATE OF CORRECTION

PATENT NO. : 5,151,435

DATED : September 29, 1992

INVENTOR(S) : S. Bagley, W.J. Greenlee, D.S. Dhanoa and A.A. Patchett

Page 1 of 6

It is certified that error appears in the above-identified patent and that said Letters Patent is hereby corrected as shown below:

In the Abstract, Item [57]:

Structural formula I should appear as follows:

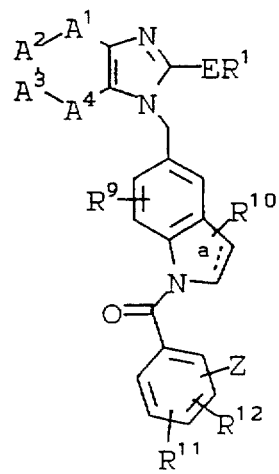

UNITED STATES PATENT AND TRADEMARK OFFICE
CERTIFICATE OF CORRECTION

PATENT NO. : 5,151,435
DATED : September 29, 1992
INVENTOR(S) : S. Bagley, W.J. Greenlee, D.S. Dhanoa and A.A. Patchett It is certified that error appears in the above-identified patent and that said Letters Patent is hereby corrected as shown below:

Column 2, lines 17-35 structural formula I should read as follows:

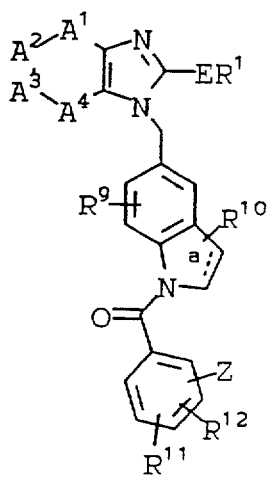

UNITED STATES PATENT AND TRADEMARK OFFICE
CERTIFICATE OF CORRECTION

PATENT NO. : 5,151,435
DATED : September 29, 1992
INVENTOR(S) : S. Bagley, W.J. Greenlee, D.S. Dhanoa and A.A. Patchett It is certified that error appears in the above-identified patent and that said Letters Patent is hereby corrected as shown below:

Column 23, line 21, the right hand structure should read as follows:

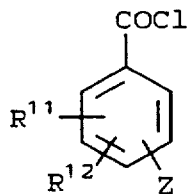

Column 24, lines 23-59, structures 2C or 3C and 4a that portion of the formula reading:

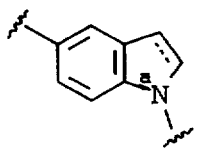 should read 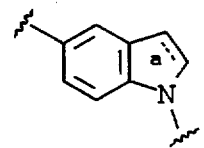

UNITED STATES PATENT AND TRADEMARK OFFICE
CERTIFICATE OF CORRECTION

PATENT NO. : 5,151,435
DATED : September 29, 1992
INVENTOR(S) : S. Bagley, W.J. Greenlee, D.S. Dhanoa and A.A. Patchett It is certified that error appears in the above-identified patent and that said Letters Patent is hereby corrected as shown below:

Column 45-46, lines 1-20; column 47-48, lines 39-55; columns 49-50, lines 1-20; column 51-52, lines 1-20; column 53-54, lines 1-20; column 55-56, lines 1-20; and column 57-58, lines 1-20 that portion of the formula reading:

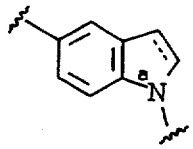 should read 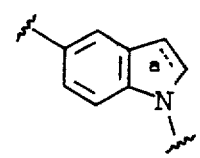 .

UNITED STATES PATENT AND TRADEMARK OFFICE
CERTIFICATE OF CORRECTION

PATENT NO. : 5,151,435
DATED : September 29, 1992
INVENTOR(S) : S. Bagley, W.J. Greenlee, D.S. Dhanoa and A.A. Patchett It is certified that error appears in the above-identified patent and that said Letters Patent is hereby corrected as shown below:

In Claim 1, column 57, lines 33-50 that portion of structural formula I reading

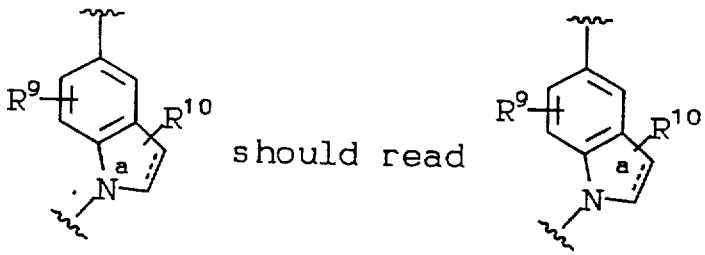

should read

UNITED STATES PATENT AND TRADEMARK OFFICE
CERTIFICATE OF CORRECTION

PATENT NO. : 5,151,435

DATED : September 29, 1992

INVENTOR(S) : S. Bagley, W.J. Greenlee, D.S. Dhanoa and A.A. Patchett

It is certified that error appears in the above-identified patent and that said Letters Patent is hereby corrected as shown below:

In Claim 4, column 66, lines 1-16 and in Claim 5, column 67, lines 1-16 that portion of the structural formula reading

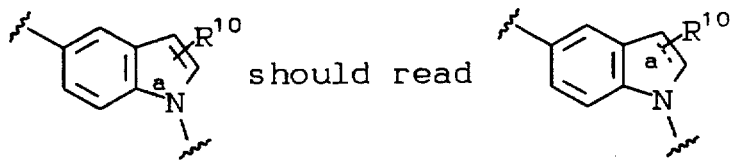

Signed and Sealed this

Twelfth Day of October, 1993

Attest:

BRUCE LEHMAN

Attesting Officer

Commissioner of Patents and Trademarks